(12) United States Patent
Gupta et al.

(10) Patent No.: US 6,770,596 B1
(45) Date of Patent: Aug. 3, 2004

(54) FUSED TRICYCLIC COMPOUNDS, PROCESS FOR THEIR PREPARATION, AND HERBICIDAL COMPOSITIONS CONTAINING THEM

(75) Inventors: Sandeep Gupta, Concord, OH (US); David A. Pulman, Mentor, OH (US); Bai-Ping Ying, Fishers, IN (US); Masamitsu Tsukamoto, Mayfield Heights, OH (US); Takahiro Haga, Kusatsu (JP)

(73) Assignee: Ishihara Sangyo Kaisha Ltd., Osaka (JP)

( * ) Notice: Subject to any disclaimer, the term of this patent is extended or adjusted under 35 U.S.C. 154(b) by 0 days.

(21) Appl. No.: 09/980,398

(22) PCT Filed: Apr. 21, 2000

(86) PCT No.: PCT/US00/08745

§ 371 (c)(1),
(2), (4) Date: Mar. 18, 2002

(87) PCT Pub. No.: WO00/73277

PCT Pub. Date: Dec. 7, 2000

(51) Int. Cl.$^7$ .................... C07D 239/22; C07D 265/28; C07D 279/22; A01N 43/54; A01N 43/84
(52) U.S. Cl. ................ 504/221; 504/225; 544/101; 544/58.6; 544/58.7
(58) Field of Search .................. 544/101, 58.6, 544/58.7; 504/225, 221

(56) References Cited

U.S. PATENT DOCUMENTS

| | | | |
|---|---|---|---|
| 4,734,124 A | 3/1988 | Chang et al. | 544/105 |
| 4,761,174 A | 8/1988 | Chang et al. | 71/92 |
| 5,084,084 A | 1/1992 | Satow et al. | 71/92 |
| 5,281,571 A | 1/1994 | Woodard et al. | 504/225 |
| 5,364,856 A | 11/1994 | Booher et al. | 514/253 |

FOREIGN PATENT DOCUMENTS

| | | |
|---|---|---|
| DE | 3927438 A1 | 2/1991 |
| EP | 0 170191 A2 | 2/1986 |
| EP | 0406993 A2 | 1/1991 |

OTHER PUBLICATIONS

Kost, L.G., et al. (M.V. Lomonosov State Univ., Moscow). Khim. Geterotsikl. Soedin., Akad Naut Latv. SSR 1996 (1), 39–45 (Russ).

*Primary Examiner*—Mukuno Shah
*Assistant Examiner*—Hong Liu
(74) *Attorney, Agent, or Firm*—Sughrue Mion, PLLC

(57) ABSTRACT

Novel fused tricyclic compounds represented by formula (I) are described. Q, Y, —L—X—, A, A', B, E, D, n and m are as defined in the disclosure. Also described are the processes for the manufacture of these compounds and agriculturally suitable compositions containing these as active ingredients which are useful as herbicides for general or selective pre-emergent or post-emergent control of undesired plant species.

12 Claims, No Drawings

FUSED TRICYCLIC COMPOUNDS, PROCESS FOR THEIR PREPARATION, AND HERBICIDAL COMPOSITIONS CONTAINING THEM

CROSS REFERENCE TO RELATED APPLICATION

This is a U.S. National Stage Application filed under 35 U.S.C. § 371 of International Application No. PCT/US00/08745 filed Apr. 21, 2000, which is a Continuation-in-part of U.S. application Ser. No. 09/323,823 filed Jun. 2, 1999, and the complete disclosures of which are incorporated into this application by reference.

The present invention relates to fused tricyclic compounds, process for their preparation, and herbicidal compositions containing them.

BACKGROUND OF THE INVENTION

It is known that some benzoxazine type compounds show herbicidal activity. They are described in U.S. Pat. No. 4,734,124, 4,761,174, 5,084,084 or 5,281,571, European Patent publication No. 0170191 or German Patent publication No. 3927438. Certain fused tricyclic compounds with herbicidal activity were described in European Patent publication No. 406993.

However, it is not known that benzoxazine type compounds with a functional group introduced at position 5 followed by cyclization afford fused tricyclic compounds which exhibit herbicidal activity.

SUMMARY OF THE INVENTION

This invention delineates a method for the control of undesired vegetation in a plantation crop by the application to the locus of the crop an effective amount of a compound described herein. The herbicidal compounds of the present invention are described by the following formula (I) or its salt:

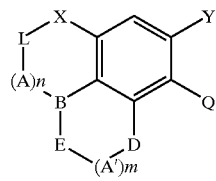

I wherein Q is a heterocycle selected from the group consisting of Q1 to Q24:

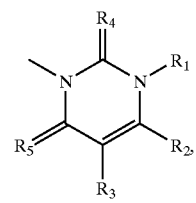

Q1

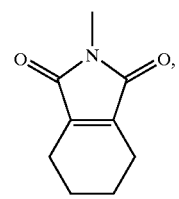

Q2

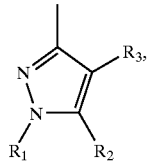

Q3

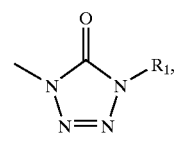

Q4

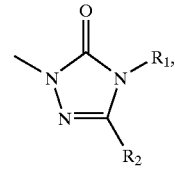

Q5

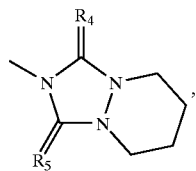

Q6

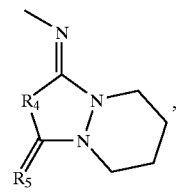

Q7

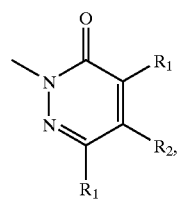

Q8

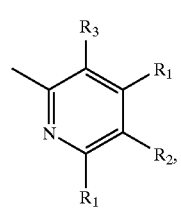

Q9

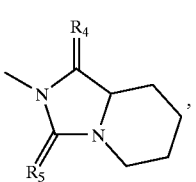

Q10

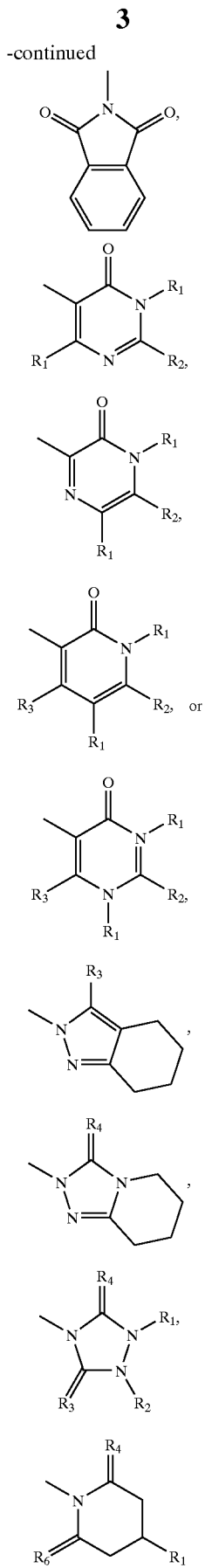
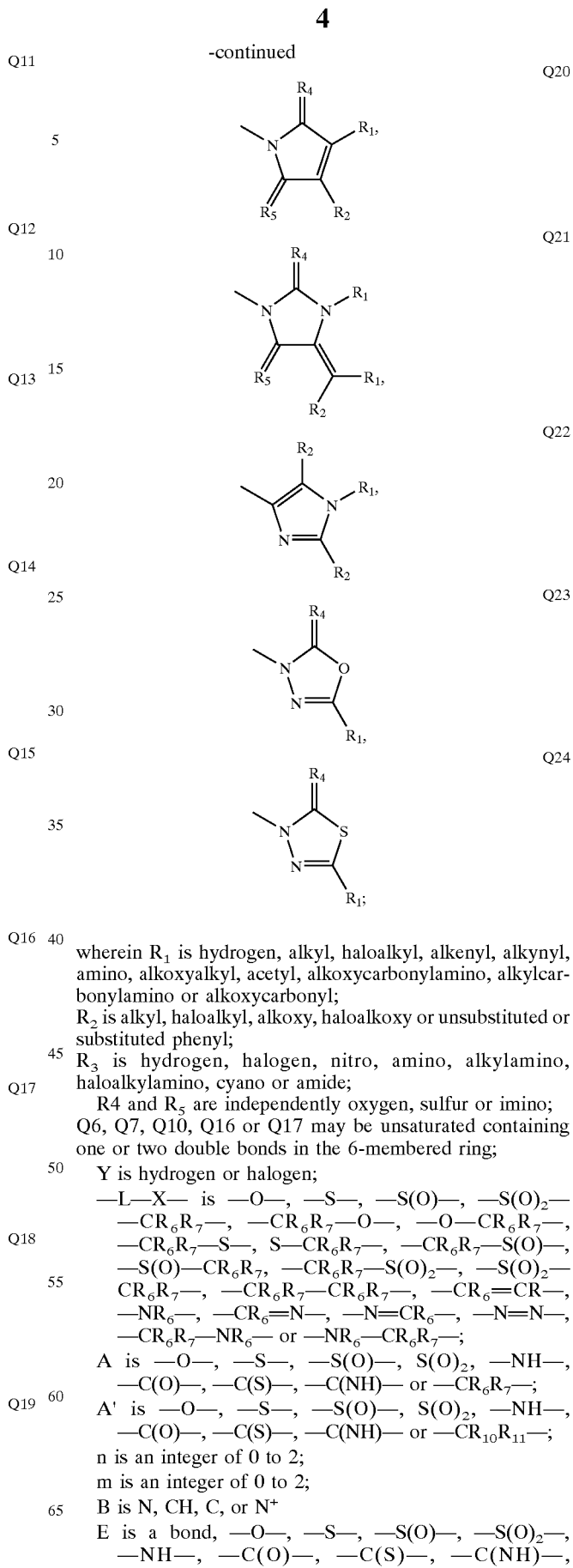

wherein $R_1$ is hydrogen, alkyl, haloalkyl, alkenyl, alkynyl, amino, alkoxyalkyl, acetyl, alkoxycarbonylamino, alkylcarbonylamino or alkoxycarbonyl;

$R_2$ is alkyl, haloalkyl, alkoxy, haloalkoxy or unsubstituted or substituted phenyl;

$R_3$ is hydrogen, halogen, nitro, amino, alkylamino, haloalkylamino, cyano or amide;

R4 and $R_5$ are independently oxygen, sulfur or imino;

Q6, Q7, Q10, Q16 or Q17 may be unsaturated containing one or two double bonds in the 6-membered ring;

Y is hydrogen or halogen;

—L—X— is —O—, —S—, —S(O)—, —S(O)$_2$— —CR$_6$R$_7$—, —CR$_6$R$_7$—O—, —O—CR$_6$R$_7$—, —CR$_6$R$_7$—S—, S—CR$_6$R$_7$—, —CR$_6$R$_7$—S(O)—, —S(O)—CR$_6$R$_7$, —CR$_6$R$_7$—S(O)$_2$—, —S(O)$_2$—CR$_6$R$_7$—, —CR$_6$R$_7$—CR$_6$R$_7$—, —CR$_6$=CR—, —NR$_6$—, —CR$_6$=N—, —N=CR$_6$—, —N=N—, —CR$_6$R$_7$—NR$_6$— or —NR$_6$—CR$_6$R$_7$—;

A is —O—, —S—, —S(O)—, S(O)$_2$, —NH—, —C(O)—, —C(S)—, —C(NH)— or —CR$_6$R$_7$—;

A' is —O—, —S—, —S(O)—, S(O)$_2$, —NH—, —C(O)—, —C(S)—, —C(NH)— or —CR$_{10}$R$_{11}$—;

n is an integer of 0 to 2;

m is an integer of 0 to 2;

B is N, CH, C, or N$^+$

E is a bond, —O—, —S—, —S(O)—, —S(O)$_2$—, —NH—, —C(O)—, —C(S)—, —C(NH)—,

—$CR_{12}R_{13}$—, —$CR_{12}R_{13}$—$CR_{12}R_{13}$—,
—$CR_{12}$=$CR_{13}$—, =$CR_{12}$— or —$NR_{12}$—;

D is —NR—, —N=$CR_{14}$—, —O—, —S—, —S(O)—, —S(O)$_2$—, —$CR_{14}R_{15}$— or —$CR_{14}$=$CR_{15}$—;

$R_6$, $R_7$, $R_8$, $R_9$, $R_{10}$, $R_{11}$, $R_{12}$, $R_{13}$, $R_{14}$ and $R_{15}$ are independently hydrogen, halogen, hydroxy, cyano, nitro, amino, alkyl, alkenyl, alkynyl, cycloalkyl, phenyl, benzyl, aryl, heteroaryl, alkoxy, haloalkoxy, aryloxy, heteroaryloxy, alkylcarbonyl, arylcarbonyl, alkoxycarbonyl, aryloxycarbonyl, amninocarbonylamino, alkylaminocarbonylamino, arylaminocarbonylamino, alkoxyalkyl, alkylthioalkyl, alkoxycarbonylalkyl, cycloalkoxycarbonylalkyl, alkylcarbonyloxyalkyl, alkylcarbonylaminoalkyl, alkoxyalkylcarbonylalkyl, heterocycloalkyl, alkylsulfonyl, arylsulfonyl, alkenylcarbonyl, alkynylcarbonyl, cycloalkylcarbonyl, heteroarylcarbonyl, alkylthiocarbonyl, cycloalkyloxycarbonyl, arylthio-carbonyl, arylthiocarbonyl, heteroaryloxycarbonyl, aminocarbonyl, alkylaminocarbonyl, arylaminocarbonyl, heteroarylaminocarbonyl, alkoxycarbonylcarbonyl or arylcarbonylcarbonyl where any of these groups may be substituted with at least one substituent selected from the group consisting of halogen, cyano, nitro, amino, dialkylamino, hydroxyl, carboxyl, alkyl, alkenyl, alkynyl, cycloalkyl, alkylcarbonyl, alkylcarbonyloxy, alkoxy, alkoxycarbonyl, alkylthio, alkylthiocarbonyl, alkoxythiocarbonyl alkylaminocarbonyl, arylaminocarbonyl, alkylsulfonyl, alkenyloxycarbonyl, alkynyloxycarbonyl, aryl, arylcarbonyl, aryloxy, aryloxycarbonyl, arylthio, heteroaryl, heteroaryloxycarbonyl and methylenedioxy, wherein the alkyl moiety or aryl moiety may be substituted with at least one substituent selected from the group consisting of halogen, cyano, nitro, alkyl, alkoxy, haloalkyl, haloalkoxy, alkoxycarbonyl, cycloalkyl, aryl and heterocycloalkyl;

R is hydrogen, alkyl alkenyl, alkynyl, cycloalkyl, cycloalkylalkyl, alkoxyalkyl, alkoxyalkoxyalkyl, alkylcarbonyl, arylcarbonyl, alkoxycarbonyl, aryloxycarbonyl, alkoxycarbonylalkyl, alkoxyalkoxycarbonylalkyl, cycloalkoxycarbonylalkyl, aralkyl, heteroaralkyl, aryloxyalkyl or heteroaryloxyalkyl where any of these groups may be substituted with at least one substituent selected from the group consisting of halogen, cyano, nitro, amino, carboxyl, alkylthioalkyl, hydroxyalkyl, $CON(R_{16})R_{17}$ and $COON(R_{16})R_{17}$;

$R_{16}$ and $R_{17}$ are independently hydrogen, halogen, alkyl, alkenyl, alkynyl, cycloalkyl, alkoxyalkyl, alkylthioalkyl, alkoxycarbonylalkyl, cycloalkoxycarbonylalkyl, alkylcarbonyloxyalkyl, alkylcarbonylaminoalkyl, alkoxyalkylcarbonylalkyl, phenyl or benzyl where any of these groups may be substituted with at least one substituent selected from the group consisting of halogen, cyano, carboxyl, hydroxy, nitro and amino.

DETAILED DESCRIPTION OF THE INVENTION

In the above definitions, the term alkyl used either alone or in compound words such as haloalkyl or alkoxy indicates either straight chain or branched alkyls containing 1–8 carbon atoms. Alkenyl and alkynyl include straight chain or branched alkenes and alkynes respectively containing 2–8 carbon atoms. The term halogen either alone or in the compound words such as haloalkyl indicates fluorine, chlorine, bromine, or iodine. Further a haloalkyl is represented by an alkyl partially or fully substituted with halogen atoms that may be same or different. A cycloalkyl group implies a saturated or unsaturated carbocycle containing 3–8 carbon atoms. A heterocycloalkyl group is a cycloalkyl group carrying 1–4 heteroatoms which are represented by oxygen, nitrogen, or sulfur atoms. An aryl group signifies an aromatic carbocycle containing 4–10 carbon atoms. A heteroaryl group is an aromatic ring containing 1–4 heteroatoms which are represented by oxygen, nitrogen, or sulfur atoms, and may for example be furanyl, pyridyl, thienyl, pyrimidinyl, benzofuranyl, quinolyl, benzothienyl or quinoxalyl.

The compound of the formula (I) may form a salt with an acidic substance or a basic substance. The salt with an acidic substance may be an inorganic acid salt such as a hydrochloride, a hydrobromide, a phosphate, a sulfate or a nitrate. The salt with a basic substance may be a salt of an inorganic or organic base such as a sodium salt, a potassium salt, a calcium salt, a quaternary ammonium salt such as ammonium salt or a dimethylamine salt.

The compound of the formula (I) may exist as geometrical or optical isomers and the present invention includes all of these isomeric forms.

Preferred compounds for the reasons of ease of synthesis or greater herbicidal efficacy are represented by the formula (I) wherein; (1) the formula (I) is

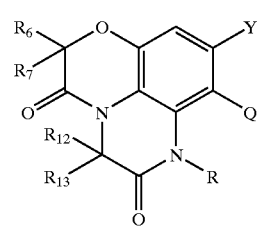

I-1

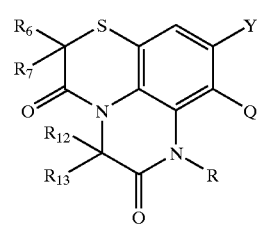

I-2

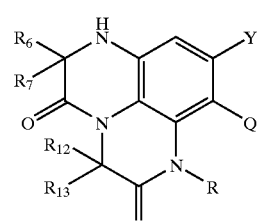

I-3

-continued

I-4
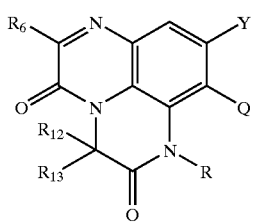

I-5
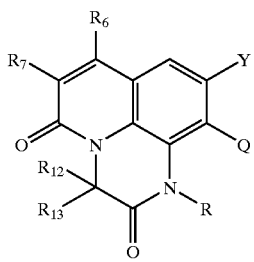

I-6
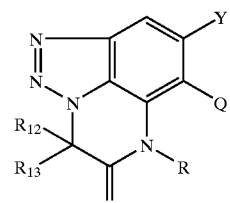

I-7
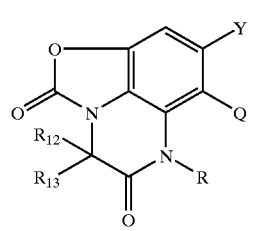

I-8
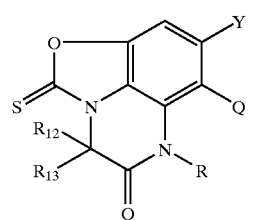

I-9
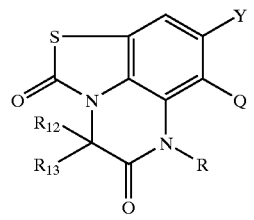

I-10
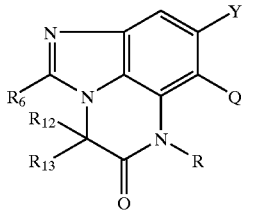

-continued

I-11
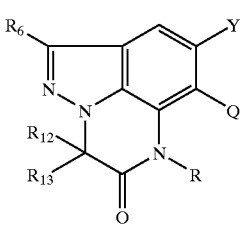

Wherein Q, R, $R_6$, $R_7$, $R_{12}$, $R_{13}$ and Y are the same as defined above;

(2) Q is Q1-5, Q16 or Q17;

(3) Y is fluorine;

More preferred is a compound of the formula (I-1)

I-1
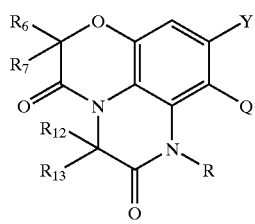

Wherein Q is Q1 or Q3; Y is fluorine; and R, $R_6$, $R_7$, $R_{12}$ and $R_{13}$ are the same as defined above.

Specific examples of preferred compounds are as follows:

8-[1-Methyl-6-(trifluoromethyl)-2,4-(1H, 3H)-pyrimidinedione-3-yl]-9-fluoro-5H-pyrazino[1,2,3-de]-1,4-benzoxazine-3,6-(2H, 7H)dione (1-1), 8-[4-Chloro-1-methyl-5-(trifluoromethyl)-1H-pyrazol-3-yl]-9-fluoro-5H-pyrazino[1,2,3-de]-1,4-benzoxazine-3,6(2H, 7H)-dione (1-13), 8-[4-Chloro-5-(difluoromethoxy)-1-methyl-1H-pyrazole-3-yl)-9-fluoro-5H-pyrazino[1,2,3-de]-1,4-benzoxazine-3,6(2H, 7H)-dione (1-25), 9-Flouro-8-(4,5,6,7-tetrahydro-2H-isoindole-1,3-dione-2-yl)-5H-pyrazino[1,2,3de]-1,4-benzoxazine-3,6(2H, 7H)-dione (1-37), 8-[4-Chloro-1-methyl-5-trifluoromethyl)-1H-pyrazol-3-yl]-]-9-fluoro-2-R-methyl-5H-pyrazino[1,2,3-de-1,4-benzoxazine-3,6(2, 7H)-dione (1-48), 8-[4-Chloro-1-methyl-5-(trifluoromethyl)-1H-pyrazol-3-yl]-2,2-dimethyl-9-fluoro-5H-pyrazino[1,2,3-de]-1,4-benzoxazine-3,6(2H, 7H)-dione (1-52) and 8-[-4-Chloro-5-(difluoromethoxy)-1-methyl-1H-pyrazol-3-yl)-9-fluoro-2-R-methyl-5H-pyrazino[1,2,3-de]-1,4-benzoxazine-3,6(2H, 7H)-dione (1-55).

The compound of the formula (I) can be produced, for example, by the following methods A to D:

A

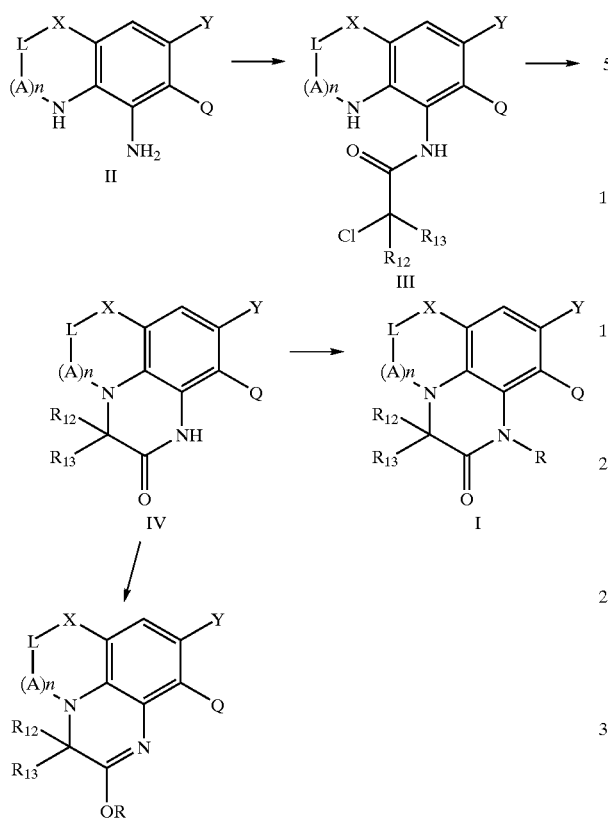

In the above formulas, Q, R, —L—X—, Y, n, $R_6$, $R_7$, $R_{12}$, $R_{13}$ and A are the same as defined previously.

The reactive derivative of $R_{12}(R_{13})C(Cl)COOH$ may, for example, be a compound selected from the group consisting of an alkyl halide, alkyl acid halide, aryl acid halide, alkyl acid anhydride, aryl acid anhydride, alkylhaloformate, alkyl isocyanate, aryl isocyanate, alkyl dihalide, aliphatic aldehyde, aliphatic ketone, aromatic aldehyde, and aromatic ketone.

The reaction is conducted usually in the presence of a solvent, if necessary, in the presence of a base. The solvent may, for example, be an aromatic hydrocarbon such as benzene or toluene: an ether such as diethyl ether, tetrahydrofuran or dioxane; a halogenated hydrocarbon such as methylene chloride or chloroform; an aprotic polar solvent such as acetonitrile, dimethylformamide or pyridine. The base may, for example, be a tertiary amine such as trimethylamine, triethylamine; a pyridine; an alkali metal hydroxide such as sodium hydroxide or potassium hydroxide; an alkali metal carbonate such as sodium carbonate or potassium carbonate; or an alkali metal alkoxide such as sodium methoxide or sodium ethoxide.

The reaction temperature is usually from 50° to +150° C., preferably from 0° to 100° C. The reaction time is form 0.1 to 24 hours.

The cyclization reaction is carried out usually in a solvent under anhydrous conditions in the presence of a base. The solvent may, for example, be an aromatic hydrocarbon such as benzene or toluene; an ether such as diethyl ether, tetrahydrofuran or dioxane; a halogenated hydrocarbon such as methylene chloride or chloroform; an aprotic polar solvent such as acetonitrile, dimethylformamide or pyridine.

The base may, for example, be a tertiary amine such as trimethylamine, triethylamine, N,N-diisopropylethylamine; a pyridine; an alkali metal hydroxide such as sodium hydroxide or potassium hydroxide; an alkali metal carbonate such as sodium carbonate or potassium carbonate; an alkali metal alkoxide such as sodium methoxide or sodium ethoxide, or an alkali metal hydride such as sodium hydride or potassium hydride. Alkali metal halides such as sodium iodide, potassium iodide may be used as catalysts.

B

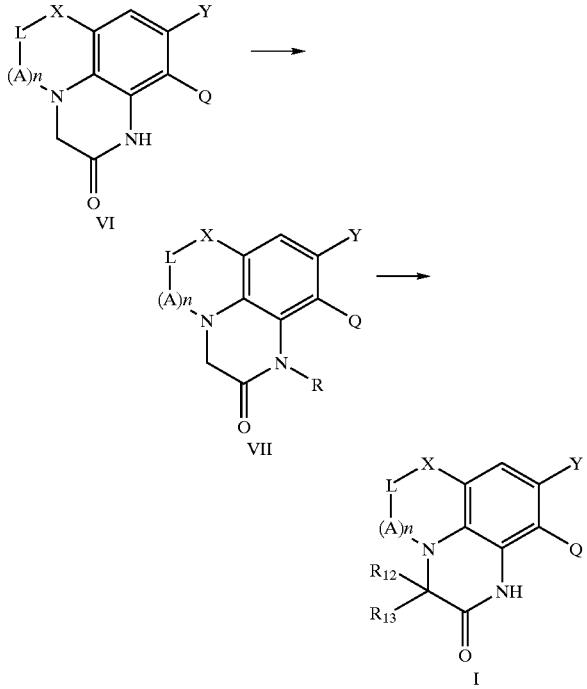

In the above formulas, Q, R, A, —L—X—, Y, $R_{12}$, $R_{13}$ and n are the same as defined above.

C

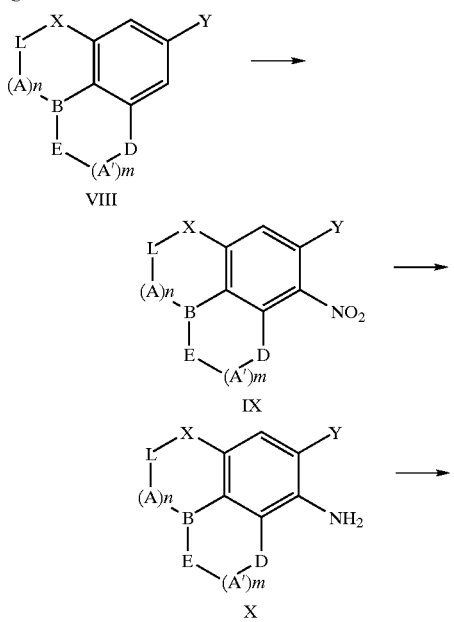

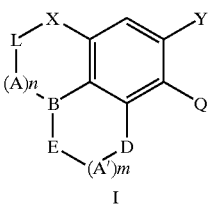

In the above formulas, Q, A, A', B, E, D, —L—X—, Y, n and m are the same as defined above.

The above nitration reaction is carried out in nitric acid or fuming nitric acid which may be mixed with sulfuric acid or acetic acid. The amount of nitric acid is usually from 1 to 100 moles per one mole of the compound of the formula (VIII).

The reaction temperature is usually from 0° to 100° C. The reaction time is form 0.1 to 24 hours.

The above reduction reaction is carried out by treatment with iron in acetic acid or ethanolic hydrochloric acid, or by hydrogenation using palladium on carbon or platinum oxide as catalyst.

The reaction temperature is usually from 0° to 50° C. The reaction time is from 0.1 to 24 hours.

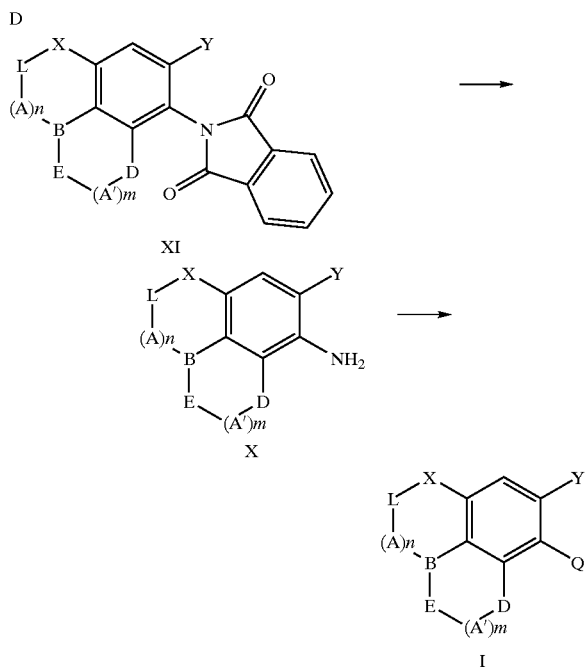

In the above formulas, Q, A, A', B, E, D, —L—X—, Y, n and m are the same as defined above.

The reaction for the formation of X from XI is carried out in a solvent such as dimethylsulfoxide, tetrahydrofuran, or dioxane in the presence of a base such as hydrazine. The reaction temperature is usually from 0° to 100° C. The reaction time is from 0.1 to 24 hours.

Now, the present invention will be described with reference to Examples. However, it should be understood that the present invention is by no means restricted by these specific Examples.

EXAMPLE 1

Preparation of 5-(2-Chloroacetylamino)-6-[4-chloro-1-methyl-5-(trifluoromethyl)-1H-pyrazol-3-yl]-7-fluoro-2H-1,4-benzoxazine-3(4H)-one.

4-Chloro-3-[7-fluoro-5-amino-2H-1,4-benzoxazine-3(4H)-on-6-yl]-1-methyl-5-trifluoromethyl-1H-pyrazole (400 mg, 1.10 mmol) was dissolved in anhydrous dioxane and chloroacetyl chloride (139.5 mg, 1.20 mmol) was added. Solution was heated to reflux for 2 hr and solvent removed in vacuo. The residue was washed with ether to afford the title compound (410 mg, 0.93 mmol).

EXAMPLE 2

Preparation of 8-[4-Chloro-1-methyl-5-(trifluoromethyl)-1H-pyrazol-3-yl]-9-fluoro-5H-pyrazino[1,2,3-de]-1,4-benzoxazine-3,6(2H, 7H)-dione (Compound No. 1-13).

4-Chloro-3-[7-fluoro-5-(2-chloroacetylamino)-2H-1,4-benzoxazine-3(4H)-on-6-yl ]-1-methyl-5-trifluoroznethyl-1H-pyrazole (250 mg, 0.57 mmol) was dissolved in anhydrous dimethylformamide (10 ml) and solution stirred under ice-cooling. Sodium hydride (16.4 mg, 95%, 0.65 mmol) was slowly added in portions and solution allowed to stir at ambient temperature for 2 hr. Solution was then added to ice-water and product extracted with ethyl acetate. Product was purified by flash chromatography on silica gel with hexane ethyl acetate (6:4) as eluent (130.4 mg, 0.32 mmol); MS ESI (negative ion) 403 $(M-1)^-$.

EXAMPLE 3

Preparation of 4-chloro-3-[7-fluoro-5-(2-chloropropionylamino)-2H-1,4-benzoxazine-3(4H)-on-6-yl]-1-methyl-5-difluoromethoxy-1H-pyrazole.

4-Chloro-3-[7-fluoro-5-amino-2H-1,4-benzoxazine-3(4H)-on-yl]-1-methyl-5-difluoromethoxy-1H-pyrazole (400 mg, 1.10mmol) was dissolved anhydrous dioxane (10 ml) and 2-chloropropionyl chloride (158.4 mg, 97%, 1.21 mmol) was added. Solution was heated to reflux for 2 hr and solvent evaporated in vacuo. The residue was washed with ether to furnish the title compound (408.3 mg, 0.90 mmol).

EXAMPLE 4

Preparation of 8-[4-Chloro-5-(difluoromethoxy)-1-methyl-1H-pyrazole-3-yl)-9-fluoro-5-methyl-5H-pyrazino[1,2,3-de]-1,4-benzoxazine-3,6(2H, 7H)-dione (Compound No. 1-26).

4-Chloro-3-[7-fluoro-5-(2-chloropropionylamino)-2H-1,4-benzoxazine-3(4H)-on-6yl]-1-methyl-5-difluoromethoxy-1H-pyrazole (300 mg, 0.66 mmol) was dissolved in anhydrous dimethylformamide (10 ml) and solution stirred under ice-cooling. Sodium hydride (20 mg, 95%, 0.79 mmol) was added slowly in portions and solution stirred at room temperature for 2 hr. Solution was then added to ice-water and product extracted with ethyl acetate. Evaporation of the solvent afforded a residue which was purified by flash chromatography on silica gel in hexane-ethyl acetate (1:1) to furnish the title compound (209.2 mg, 0.50 mmol).

EXAMPLE 5

Preparation of 3-[5-(2-chloroacetylamino)-7-fluoro-2H-1,4-benzoxazine-3(4H)-on-6-yl]-1-methyl-6-trifluoromethyl-2,4-(1H,3H)-pyrimidinedione.

3-[5-Amino-7-fluoro-2H-1,4-benzoxazine-3(4H)-on-6-yl]-1-methyl-6-trifluoromethyl-2,4-(1H,3H)-pyrimidinedione (400 mg, 1.07 mmol) was dissolved in anhydrous dioxane and chloroacetyl chloride (135.6 mg, 1.20 mmol) was added. Solution was heated to reflux for 2 hr and solvent removed in vacuo. The residue was washed with ether to afford the title compound (351.9 mg, 0.78 mmol).

EXAMPLE 6

Preparation of 8-[1-methyl-6-(trifluoromethyl)-2,4-(1H, 3H)-pyrimidinedione-3-yl]-9-fluoro-5H-pyrazino[1,2,3-de]-1,4-benzoxazine-3,6-(2H, 7H)-dione (1-1).

3-[5-(2-Chloroacetylamino)-7-fluoro-2H-1,4-benzoxazine-3(4H)-on-6-yl]-1-methyl-6-trifluoromethyl-2,4-(1H,3H)-pyrimidinedione (271 mg, 0.60 mmol was dissolved in anhydrous acetonitrile (10 ml) and potassium iodide (14 mg, 0.08 mmol) and N,N-diisopropylethylamine (100.8 mg, 0.78 mmol) were added. Solution was refluxed for 2 hr. added to water and extracted with ethyl acetate. Product was purified by flash chromatography on silica gel with hexane-ethyl acetate (1:1) as eluent (218.6 mg, 0.53 mmol).

EXAMPLE 7

Preparation of Methyl-2-R-[4-[4-chloro-1-methyl-5-trifluoromethyl)-1H-pyrazol-3-yl]-5-fluoro-2-nitrophenoxy]propanoate.

2,4-Difluoro-5-[4-chloro-1-methyl-5-(trifluoromethyl) 1H-pyrazol-3-yl]-nitrobenzene (5.0 g, 14.63 mmol) and methyl (R)-(+)-lactate (1.71 g, 16.10 mmol) were dissolved in anhydrous tetrahydrofuran (73 ml) and stirred under ice cooling. Sodium hydride (406.7 mg, 95%, 16.10 mmol) was added in portions and solution stirred at ambient temperature for 2 hr. Solution was then added to ice water and product separated by filtration (6.1 g, 14.33 mmol).

EXAMPLE 8

Preparation of 7-Fluoro-6-[4-chloro-1-methyl-5-(trifluoromethyl)-1H-pyrazol-3-yl]-2-R-methyl-2H-1,4-benzoxazine-3(4H)-one.

Methyl-2-R-[4-[4-chloro-1-methyl-5-(trifluoromethyl)-1H-pyrazol-3-yl]-5-fluoro-2-nitrophenoxy]propanoate (6.0 g, 14.09 mmol) was dissolved in glacial acetic acid (140 ml) and reduced iron powder (3.94 g, 70.45 mmol) was added. Solution was stirred at 80° C. under an atmosphere of nitrogen for 2 hr. Water was added and the product extracted with ethyl acetate, washed with water and dried (anhydrous sodium sulfate). Evaporation of solvent afforded the title compound (5.0 g, 13.74 mmol).

EXAMPLE 9

Preparation of 7-Fluoro-6-[4-chloro-1-methyl-5-(trifluoromethyl)-1H-pyrazol-3-yl]-2-R-methyl-5-nitro-2H-1,4-benzoxazine-3(4H)-one.

7-Fluoro-6-[4chloro-1-methyl-5-(trifluoromethyl)-1H-pyrazol-3-yl]-2-R-methyl-2H-1,4-benzoxazine-3(4H)-one (2.5 g, 6.87 mmol) was dissolved in glacial acetic acid (52 ml) and fuming nitric acid (20.8 ml) was slowly added with stirring. Solution was stirred at ambient temperature for 2 hr. Ice water was added and the product separated by filtration (2.29 g, 5.60 mmol).

EXAMPLE 10

Preparation of 5-Amino-7-fluoro-6-[4-chloro-1-methyl-5-(trifluoromethyl)-1H-pyrazol-3-yl]-2-R-methyl-2H-1,4-benzoxazine-3(4H)-one.

7-Fluoro-6-[4-chloro-1-methyl-5-(trifluoromethyl)-1H-pyrazol-3-yl]-2-R-methyl-5-nitro-2H-1,4-benzoxazine-3 (4H)-one (2.29 g, 5.6 mmol) was dissolved in glacial acetic acid (56 ml) and reduced iron powder (1.56 g, 28.0 mmol) was added in portions. Solution was stirred at ambient temperature for 16 hr and water was added. Product was extracted with ethyl acetate and washed with water and brine. Evaporation of solvent furnished a residue, which was triturated with ether to afford the title compound (1.79 g. 4.73 mmol).

EXAMPLE 11

Preparation of 5-(2-Chloroacetylamino)-6-[4-chloro-1-methyl-5-(trifluoromethyl)-1H-pyrazol-3-yl]-7-fluoro-2-R-methyl-2H-1,4-benzoxazine-3(4H)-one.

5-Amino-7-fluoro-6-[4-chloro-1-methyl-5 (trifuoromethyl)-1H-pyrazol-3-yl]-2-R-methyl-2H-1,4-benzoxazine-3(4H)-one (1.0 g. 2.64 mmol) was dissolved in anhydrous dioxane (40 ml) and chloroacetyl chloride (0.34 g, 3.01 mmol) was added. Solution was refluxed for 2 hr and solvent was then evaporated. The residue was triturated with ether to afford the title compound (0.90 g, 1.98 mmol).

EXAMPLE 12

Preparation of 8-[4-Chloro-1-methyl-5-(trifluoromethyl)-1H-pyrazol-3-yl]-9-fluoro-2-R-methyl-5H-pyrazino[1,2,3-de]-1,4-benzoxazine-3,6 (2H, 7H)-dione (Compound No. 1-48).

5-(2-Chloroacetylamino)-6-[4-chloro-1-methyl-5-(trifluoromethyl)-1H-pyrazol-3-yl]-7-fluoro-2-R-methyl-2H-1,4-benzoxazine-3(4H)-one (0.90 g, 1.98 mmol) was dissolved in anhydrous dimethylformamide (20 ml) and stirred under ice cooling. Sodium hydride (52.3 mg, 2.18 mmol) was added in portions. Solution was stirred at ambient temperature for 2 hr and added to ice water. Product was separated by filtration (0.66 g, 1.58 mmol). $^1$H NMR data for the compound are listed in Table 4.

The corresponding enantiomeric compound 8-[4-Chloro-1-methyl-5-(trifluoromethyl)-1H-pyrazol-3-yl]-9-fluoro-2-S-methyl-5H-pyrazino[1,2,3-de]-1,4-benzoxazine-3,6(2H, 7H)-dione (Compound No. 1-49) was prepared in an identical fashion starting from methyl (S)-(−)-lactate. The product was determined to be chirally enriched by the NMR analysis using chiral Lanthanide Shift Reagent (LSR). Chirality is retained in the products (Compound Nos. 1-48 and 1-49). This was confirmed by NMR analysis of the two compounds with chiral LSR europium tris[3-(heptafluoropropylhydroxymethylene)-(+)-camphorate] [Eu (HFC)$_3$]. In the presence of LSR (molar ratio 1:1) in deuterated chloroform (0.015 mmol solution), the two methyls in compound no. 1-48 (N—CH$_3$, 4.02 ppm; CH—CH$_3$, 3.53 ppm) and compound no. 1-49 (N—CH$_3$, 4.06 ppm; CH—CH$_3$, 3.40 ppm) appear as single set of signals. These resonances in the equimolar mixture of compound no. 1-48 and compound no. 1-49, in the presence of the LSR, are resolved as distinct pairs.

EXAMPLE 13

Preparation of 5-(2-Bromoisobutyrylamino)-6-[4chloro-1-methyl-5-(trifluoromethyl)-1H-pyrazol-3-yl]-7-fluoro-2H-1,4benzoxazine-3(4H)-one.

5-Amino-7-fluoro-6-[4-chloro-1-methyl-5-(trifluoromethyl)-1H-pyrazol-3-yl]-2H-1,4-benzoxazine-3 (4H)-one (1.0 g, 2.64 mmol) was dissolved in anhydrous dioxane (40 ml) and 2-bromoisobutyryl bromide (0.67 g, 2.91 mmol) was added. Solution was refluxed for 2 hr and solvent was then evaporated. The residue was triturated with ether to afford the title compound (1.02 g, 1.99 mmol).

EXAMPLE 14

Preparation of 8-[4-Chloro-1-methyl-5-(trifluoromethyl)-1H-pyrazol-3-yl]-5,5-dimethyl-9-fluoro-5H-pyrazino[1,2,3-de]-1,4-benzoxazine-3,6(2H, 7H)-dione (Compound No. 1-15).

5-(2-Bromoisobutyrylamino)-6-[4-chloro-1-methyl-5-(trifluoromethyl)-1H-pyrazol-3-yl]-7-fluoro-2H-1,4-benzoxazine-3(4H)-one (1.15 g, 2.24 mmol) was dissolved in anhydrous acetonitrile (50 ml) and potassium iodide (0.45 g, 2.70 mmol) and potassium carbonate (0.37 g, 2.70 mmol) were added. Solution was refluxed for 2 hr and water was added. Product was extracted with ethyl acetate and solvent evaporated. Column chromatography on silica gel using hexane-ethyl acetate (7:3) as eluent afforded the title compound (84.0 mg, 0.19 mmol).

Using the procedures as described in processes A-D and Examples 1–4, the compounds of this invention can be readily prepared. Tables 1–3 list structures for few representative examples of this invention.

TABLE 1

| No. | Y | R | $R_6$ | $R_7$ | $R_{12}$ | $R_{13}$ | Q | $R_1$ | $R_2$ | $R_3$ | $R_4$ | $R_5$ |
|---|---|---|---|---|---|---|---|---|---|---|---|---|
| 1-1 | F | H | H | H | H | H | Q1 | $CH_3$ | $CF_3$ | H | O | O |
| 1-2 | F | H | H | H | H | $CH_3$ | Q1 | $CH_3$ | $CF_3$ | H | O | O |
| 1-3 | F | H | H | H | $CH_3$ | $CH_3$ | Q1 | $CH_3$ | $CF_3$ | H | O | O |
| 1-4 | F | H | H | H | H | $CH_2CH_3$ | Q1 | $CH_3$ | $CF_3$ | H | O | O |
| 1-5 | F | H | H | H | $CH_2CH_3$ | $CH_2CH_3$ | Q1 | $CH_3$ | $CF_3$ | H | O | O |
| 1-6 | F | H | H | H | H | $CH_2Cl$ | Q1 | $CH_3$ | $CF_3$ | H | O | O |
| 1-7 | F | H | H | H | H | $CH_2OCH_3$ | Q1 | $CH_3$ | $CF_3$ | H | O | O |
| 1-8 | F | H | H | H | H | $CH=CH_2$ | Q1 | $CH_3$ | $CF_3$ | H | O | O |
| 1-9 | F | H | H | H | H | phenyl | Q1 | $CH_3$ | $CF_3$ | H | O | O |
| 1-10 | F | H | H | H | phenyl | phenyl | Q1 | $CH_3$ | $CF_3$ | H | O | O |
| 1-11 | F | $CH_3$ | H | H | H | H | Q1 | $CH_3$ | $CF_3$ | H | O | O |
| 1-12 | F | H | H | H | H | H | Q1 | $NH_2$ | $CF_3$ | H | O | O |
| 1-13 | F | H | H | H | H | H | Q3 | $CH_3$ | $CF_3$ | Cl | — | — |
| 1-14 | F | H | H | H | H | $CH_3$ | Q3 | $CH_3$ | $CF_3$ | Cl | — | — |
| 1-15 | F | H | H | H | $CH_3$ | $CH_3$ | Q3 | $CH_3$ | $CF_3$ | Cl | — | — |
| 1-16 | F | H | H | H | H | $CH_2CH_3$ | Q3 | $CH_3$ | $CF_3$ | Cl | — | — |
| 1-17 | F | H | H | H | $CH_2CH_3$ | $CH_2CH_3$ | Q3 | $CH_3$ | $CF_3$ | Cl | — | — |
| 1-18 | F | H | H | H | H | $CH_2Cl$ | Q3 | $CH_3$ | $CF_3$ | Cl | — | — |
| 1-19 | F | H | H | H | H | $CH_2OCH_3$ | Q3 | $CH_3$ | $CF_3$ | Cl | — | — |
| 1-20 | F | H | H | H | H | $CH=CH_2$ | Q3 | $CH_3$ | $CF_3$ | Cl | — | — |
| 1-21 | F | H | H | H | H | phenyl | Q3 | $CH_3$ | $CF_3$ | Cl | — | — |
| 1-22 | F | H | H | H | phenyl | phenyl | Q3 | $CH_3$ | $CF_3$ | Cl | — | — |
| 1-23 | F | $CH_3$ | H | H | H | H | Q3 | $CH_3$ | $CF_3$ | Cl | — | — |
| 1-24 | F | H | H | H | H | H | Q3 | $CH_3$ | $CF_3$ | Br | — | — |
| 1-25 | F | H | H | H | H | H | Q3 | $CH_3$ | $OCHF_2$ | Cl | — | — |
| 1-26 | F | H | H | H | H | $CH_3$ | Q3 | $CH_3$ | $OCHF_2$ | Cl | — | — |
| 1-27 | F | H | H | H | $CH_3$ | $CH_3$ | Q3 | $CH_3$ | $OCHF_2$ | Cl | — | — |
| 1-28 | F | H | H | H | H | $CH_2CH_3$ | Q3 | $CH_3$ | $OCHF_2$ | Cl | — | — |
| 1-29 | F | H | H | H | $CH_2CH_3$ | $CH_2CH_3$ | Q3 | $CH_3$ | $OCHF_2$ | Cl | — | — |
| 1-30 | F | H | H | H | H | $CH_2Cl$ | Q3 | $CH_3$ | $OCHF_2$ | Cl | — | — |
| 1-31 | F | H | H | H | H | $CH_2OCH_3$ | Q3 | $CH_3$ | $OCHF_2$ | Cl | — | — |
| 1-32 | F | H | H | H | H | $CH=CH_2$ | Q3 | $CH_3$ | $OCHF_2$ | Cl | — | — |
| 1-33 | F | H | H | H | H | phenyl | Q3 | $CH_3$ | $OCHF_2$ | Cl | — | — |
| 1-34 | F | H | H | H | phenyl | phenyl | Q3 | $CH_3$ | $OCHF_2$ | Cl | — | — |
| 1-35 | F | $CH_3$ | H | H | H | H | Q3 | $CH_3$ | $OCHF_2$ | Cl | — | — |
| 1-36 | F | H | H | H | H | H | Q3 | $CH_3$ | $OCHF_2$ | Br | — | — |
| 1-37 | F | H | H | H | H | H | Q2 | — | — | — | — | — |
| 1-38 | F | H | H | H | H | $CH_3$ | Q2 | — | — | — | — | — |
| 1-39 | F | H | H | H | $CH_3$ | $CH_3$ | Q2 | — | — | — | — | — |
| 1-40 | F | H | H | H | H | $CH_2CH_3$ | Q2 | — | — | — | — | — |
| 1-41 | F | H | H | H | $CH_2CH_3$ | $CH_2CH_3$ | Q2 | — | — | — | — | — |
| 1-42 | F | H | H | H | H | $CH_2Cl$ | Q2 | — | — | — | — | — |
| 1-43 | F | H | H | H | H | $CH_2OCH_3$ | Q2 | — | — | — | — | — |
| 1-44 | F | H | H | H | H | $CH=CH_2$ | Q2 | — | — | — | — | — |
| 1-45 | F | H | H | H | H | phenyl | Q2 | — | — | — | — | — |
| 1-46 | F | H | H | H | phenyl | phenyl | Q2 | — | — | — | — | — |
| 1-47 | F | $CH_3$ | H | H | H | H | Q2 | — | — | — | — | — |
| 1-48 | F | H | H | R-$CH_3$ | H | H | Q3 | $CH_3$ | $CF_3$ | Cl | — | — |
| 1-49 | F | H | H | S-$CH_3$ | H | H | Q3 | $CH_3$ | $CF_3$ | Cl | — | — |

TABLE 1-continued

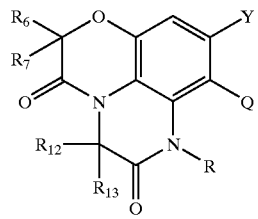

| No. | Y | R | R$_6$ | R$_7$ | R$_{12}$ | R$_{13}$ | Q | R$_1$ | R$_2$ | R$_3$ | R$_4$ | R$_5$ |
|---|---|---|---|---|---|---|---|---|---|---|---|---|
| 1-50 | F | H | H | R-CH$_3$ | H | CH$_3$ | Q3 | CH$_3$ | CF$_3$ | Cl | — | — |
| 1-51 | F | H | H | S-CH$_3$ | H | CH$_3$ | Q3 | CH$_3$ | CF$_3$ | Cl | — | — |
| 1-52 | F | H | CH$_3$ | CH$_3$ | H | H | Q3 | CH$_3$ | CF$_3$ | Cl | — | — |
| 1-53 | F | H | H | R-CH$_3$ | H | CH(CH$_3$)$_2$ | Q3 | CH$_3$ | CF$_3$ | Cl | — | — |
| 1-54 | F | H | CH$_3$ | CH$_3$ | H | CH$_3$ | Q3 | CH$_3$ | CF$_3$ | Cl | — | — |
| 1-55 | F | H | H | R-CH$_3$ | H | H | Q3 | CH$_3$ | OCHF$_2$ | Cl | — | — |
| 1-56 | F | H | H | S-CH$_3$ | H | H | Q3 | CH$_3$ | OCHF$_2$ | Cl | — | — |
| 1-57 | F | H | H | R-CH$_3$ | H | CH$_3$ | Q3 | CH$_3$ | OCHF$_2$ | Cl | — | — |
| 1-58 | F | H | H | S-CH$_3$ | H | CH$_3$ | Q3 | CH$_3$ | OCHF$_2$ | Cl | — | — |
| 1-59 | F | H | CH$_3$ | CH$_3$ | H | H | Q3 | CH$_3$ | OCHF$_2$ | Cl | — | — |
| 1-60 | F | H | CH$_3$ | CH$_3$ | H | CH$_3$ | Q3 | CH$_3$ | OCHF$_2$ | Cl | — | — |
| 1-61 | F | H | CH$_3$ | CH$_3$ | H | CH$_2$CH$_3$ | Q3 | CH$_3$ | OCHF$_2$ | Cl | — | — |
| 1-62 | F | CH$_3$ | H | H | H | CH$_3$ | Q3 | CH$_3$ | OCHF$_2$ | Cl | — | — |
| 1-63 | F | H | H | H | H | H | Q9 | H | CF$_3$ | Cl | — | — |
| 1-64 | F | H | H | H | H | CH$_3$ | Q9 | H | CF$_3$ | Cl | — | — |
| 1-65 | F | H | H | H | CH$_3$ | CH$_3$ | Q9 | H | CF$_3$ | Cl | — | — |
| 1-66 | F | H | H | H | H | CH$_2$CH$_3$ | Q9 | H | CF$_3$ | Cl | — | — |
| 1-67 | F | H | H | H | CH$_2$CH$_3$ | CH$_2$CH$_3$ | Q9 | H | CF$_3$ | Cl | — | — |
| 1-68 | F | H | H | H | H | phenyl | Q9 | H | CF$_3$ | Cl | — | — |
| 1-69 | F | H | H | CH$_3$ | H | H | Q9 | H | CF$_3$ | Cl | — | — |
| 1-70 | F | H | H | CH$_3$ | H | CH$_3$ | Q9 | H | CF$_3$ | Cl | — | — |
| 1-71 | F | H | CH$_3$ | CH$_3$ | H | H | Q9 | H | CF$_3$ | Cl | — | — |
| 1-72 | F | H | CH$_3$ | CH$_3$ | H | CH$_3$ | Q9 | H | CF$_3$ | Cl | — | — |
| 1-73 | F | H | H | H | H | H | Q5 | CHF$_2$ | CH$_3$ | — | — | — |
| 1-74 | F | H | H | H | H | CH$_3$ | Q5 | CHF$_2$ | CH$_3$ | — | — | — |
| 1-75 | F | H | H | H | H | CH$_2$CH$_3$ | Q5 | CHF$_2$ | CH$_3$ | — | — | — |
| 1-76 | F | H | H | H | H | H | Q4 | (CH$_2$)$_3$F | — | — | — | — |
| 1-77 | F | H | H | H | H | CH(CH$_3$)$_2$ | Q1 | CH$_3$ | CF$_3$ | H | O | O |
| 1-78 | F | H | H | H | H | CH(CH$_3$)$_2$ | Q2 | — | — | — | — | — |
| 1-79 | F | H | H | H | H | Cl | Q3 | CH$_3$ | OCHF$_2$ | Cl | — | — |

TABLE 2

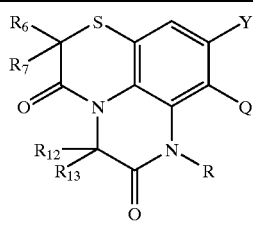

| No. | Y | R | R$_4$ | R$_7$ | R$_{12}$ | R$_{13}$ | Q | R$_1$ | R$_2$ | R$_3$ | R$_4$ | R$_5$ |
|---|---|---|---|---|---|---|---|---|---|---|---|---|
| 2-1 | F | H | H | H | H | H | Q1 | CH$_3$ | CF$_3$ | H | O | O |
| 2-2 | F | H | H | H | H | CH$_3$ | Q1 | CH$_3$ | CF$_3$ | H | O | O |
| 2-3 | F | H | H | H | CH$_3$ | CH$_3$ | Q1 | CH$_3$ | CF$_3$ | H | O | O |
| 2-4 | F | H | H | H | H | CH$_2$CH$_3$ | Q1 | CH$_3$ | CF$_3$ | H | O | O |
| 2-5 | F | H | H | H | CH$_2$CH$_3$ | CH$_2$CH$_3$ | Q1 | CH$_3$ | CF$_3$ | H | O | O |
| 2-6 | F | H | H | H | H | CH$_2$Cl | Q1 | CH$_3$ | CF$_3$ | H | O | O |
| 2-7 | F | H | H | H | H | CH$_2$OCH$_3$ | Q1 | CH$_3$ | CF$_3$ | H | O | O |
| 2-8 | F | H | H | H | H | CH=CH$_2$ | Q1 | CH$_3$ | CF$_3$ | H | O | O |
| 2-9 | F | H | H | H | H | phenyl | Q1 | CH$_3$ | CF$_3$ | H | O | O |
| 2-10 | F | H | H | H | phenyl | phenyl | Q1 | CH$_3$ | CF$_3$ | H | O | O |
| 2-11 | F | CH$_3$ | H | H | H | H | Q1 | CH$_3$ | CF$_3$ | H | O | O |
| 2-12 | F | H | H | H | H | H | Q1 | NH$_2$ | CF$_3$ | H | O | O |
| 2-13 | F | H | H | H | H | H | Q3 | CH$_3$ | CF$_3$ | Cl | — | — |
| 2-14 | F | H | H | H | H | CH$_3$ | Q3 | CH$_3$ | CF$_3$ | Cl | — | — |
| 2-15 | F | H | H | H | CH$_3$ | CH$_3$ | Q3 | CH$_3$ | CF$_3$ | Cl | — | — |
| 2-16 | F | H | H | H | H | CH$_2$CH$_3$ | Q3 | CH$_3$ | CF$_3$ | Cl | — | — |
| 2-17 | F | H | H | H | CH$_2$CH$_3$ | CH$_2$CH$_3$ | Q3 | CH$_3$ | CF$_3$ | Cl | — | — |

TABLE 2-continued

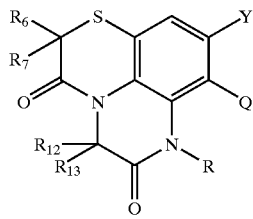

| No. | Y | R | R$_4$ | R$_7$ | R$_{12}$ | R$_{13}$ | Q | R$_1$ | R$_2$ | R$_3$ | R$_4$ | R$_5$ |
|---|---|---|---|---|---|---|---|---|---|---|---|---|
| 2-18 | F | H | H | H | H | CH$_2$Cl | Q3 | CH$_3$ | CF$_3$ | Cl | — | — |
| 2-19 | F | H | H | H | H | CH$_2$OCH$_3$ | Q3 | CH$_3$ | CF$_3$ | Cl | — | — |
| 2-20 | F | H | H | H | H | CH=CH$_2$ | Q3 | CH$_3$ | CF$_3$ | Cl | — | — |
| 2-21 | F | H | H | H | H | phenyl | Q3 | CH$_3$ | CF$_3$ | Cl | — | — |
| 2-22 | F | H | H | H | phenyl | phenyl | Q3 | CH$_3$ | CF$_3$ | Cl | — | — |
| 2-23 | F | CH$_3$ | H | H | H | H | Q3 | CH$_3$ | CF$_3$ | Cl | — | — |
| 2-24 | F | H | H | H | H | H | Q3 | CH$_3$ | CF$_3$ | Br | | |
| 2-25 | F | H | H | H | H | H | Q3 | CH$_3$ | OCHF$_2$ | Cl | — | — |
| 2-26 | F | H | H | H | H | CH$_3$ | Q3 | CH$_3$ | OCHF$_2$ | Cl | — | — |
| 2-27 | F | H | H | H | CH$_3$ | CH$_3$ | Q3 | CH$_3$ | OCHF$_2$ | Cl | — | — |
| 2-28 | F | H | H | H | H | CH$_2$CH$_3$ | Q3 | CH$_3$ | OCHF$_2$ | Cl | — | — |
| 2-29 | F | H | H | H | CH$_2$CH$_3$ | CH$_2$CH$_3$ | Q3 | CH$_3$ | OCHF$_2$ | Cl | — | — |
| 2-30 | F | H | H | H | H | CH$_2$Cl | Q3 | CH$_3$ | OCHF$_2$ | Cl | — | — |
| 2-31 | F | H | H | H | H | CH$_2$OCH$_3$ | Q3 | CH$_3$ | OCHF$_2$ | Cl | — | — |
| 2-32 | F | H | H | H | H | CH=CH$_2$ | Q3 | CH$_3$ | OCHF$_2$ | Cl | — | — |
| 2-33 | F | H | H | H | H | phenyl | Q3 | CH$_3$ | OCHF$_2$ | Cl | — | — |
| 2-34 | F | H | H | H | phenyl | phenyl | Q3 | CH$_3$ | OCHF$_2$ | Cl | — | — |
| 2-35 | F | CH$_3$ | H | H | H | H | Q3 | CH$_3$ | OCHF$_2$ | Cl | — | — |
| 2-36 | F | H | H | H | H | H | Q3 | CH$_3$ | OCHF$_2$ | Br | | |
| 2-37 | F | H | H | H | H | H | Q2 | — | — | — | — | — |
| 2-38 | F | H | H | H | H | CH$_3$ | Q2 | — | — | — | — | — |
| 2-39 | F | H | H | H | CH$_3$ | CH$_3$ | Q2 | — | — | — | — | — |
| 2-40 | F | H | H | H | H | CH$_2$CH$_3$ | Q2 | — | — | — | — | — |
| 2-41 | F | H | H | H | CH$_2$CH$_3$ | CH$_2$CH$_3$ | Q2 | — | — | — | — | — |
| 2-42 | F | H | H | H | H | CH$_2$Cl | Q2 | — | — | — | — | — |
| 2-43 | F | H | H | H | H | CH$_2$OCH$_3$ | Q2 | — | — | — | — | — |
| 2-44 | F | H | H | H | H | CH=CH$_2$ | Q2 | — | — | — | — | — |
| 2-45 | F | H | H | H | H | phenyl | Q2 | — | — | — | — | — |
| 2-46 | F | H | H | H | phenyl | phenyl | Q2 | — | — | — | — | — |
| 2-47 | F | CH$_3$ | H | H | H | H | Q2 | — | — | — | — | — |

TABLE 3

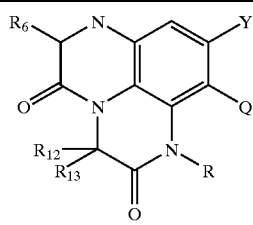

| No. | Y | R | R$_6$ | R$_{12}$ | R$_{13}$ | Q | R$_1$ | R$_2$ | R$_3$ | R$_4$ | R$_5$ |
|---|---|---|---|---|---|---|---|---|---|---|---|
| 3-1 | F | H | H | H | H | Q1 | CH$_3$ | CF$_3$ | H | O | O |
| 3-2 | F | H | H | H | CH$_3$ | Q1 | CH$_3$ | CF$_3$ | H | O | O |
| 3-3 | F | H | H | CH$_3$ | CH$_3$ | Q1 | CH$_3$ | CF$_3$ | H | O | O |
| 3-4 | F | H | H | H | CH$_2$CH$_3$ | Q1 | CH$_3$ | CF$_3$ | H | O | O |
| 3-5 | F | H | H | CH$_2$CH$_3$ | CH$_2$CH$_3$ | Q1 | CH$_3$ | CF$_3$ | H | O | O |
| 3-6 | F | H | H | H | CH$_2$Cl | Q1 | CH$_3$ | CF$_3$ | H | O | O |
| 3-7 | F | H | H | H | CH$_2$OCH$_3$ | Q1 | CH$_3$ | CF$_3$ | H | O | O |
| 3-8 | F | H | H | H | CH=CH$_2$ | Q1 | CH$_3$ | CF$_3$ | H | O | O |
| 3-9 | F | H | H | H | phenyl | Q1 | CH$_3$ | CF$_3$ | H | O | O |
| 3-10 | F | H | H | phenyl | phenyl | Q1 | CH$_3$ | CF$_3$ | H | O | O |
| 3-11 | F | CH$_3$ | H | H | H | Q1 | CH$_3$ | CF$_3$ | H | O | O |
| 3-12 | F | H | H | H | H | Q1 | NH$_2$ | CF$_3$ | H | O | O |
| 3-13 | F | H | H | H | H | Q3 | CH$_3$ | CF$_3$ | Cl | — | — |
| 3-14 | F | H | H | H | CH$_3$ | Q3 | CH$_3$ | CF$_3$ | Cl | — | — |
| 3-15 | F | H | H | CH$_3$ | CH$_3$ | Q3 | CH$_3$ | CF$_3$ | Cl | — | — |
| 3-16 | F | H | H | H | CH$_2$CH$_3$ | Q3 | CH$_3$ | CF$_3$ | Cl | — | — |
| 3-17 | F | H | H | CH$_2$CH$_3$ | CH$_2$CH$_3$ | Q3 | CH$_3$ | CF$_3$ | Cl | — | — |

TABLE 3-continued

| No. | Y | R | $R_6$ | $R_{12}$ | $R_{13}$ | Q | $R_1$ | $R_2$ | $R_3$ | $R_4$ | $R_5$ |
|---|---|---|---|---|---|---|---|---|---|---|---|
| 3-18 | F | H | H | H | $CH_2Cl$ | Q3 | $CH_3$ | $CF_3$ | Cl | — | — |
| 3-19 | F | H | H | H | $CH_2OCH_3$ | Q3 | $CH_3$ | $CF_3$ | Cl | — | — |
| 3-20 | F | H | H | H | $CH=CH_2$ | Q3 | $CH_3$ | $CF_3$ | Cl | — | — |
| 3-21 | F | H | H | H | phenyl | Q3 | $CH_3$ | $CF_3$ | Cl | — | — |
| 3-22 | F | H | H | phenyl | phenyl | Q3 | $CH_3$ | $CF_3$ | Cl | — | — |
| 3-23 | F | $CH_3$ | H | H | H | Q3 | $CH_3$ | $CF_3$ | Cl | — | — |
| 3-24 | F | H | H | H | H | Q3 | $CH_3$ | $CF_3$ | Br | | |
| 3-25 | F | H | H | H | H | Q3 | $CH_3$ | $OCHF_2$ | Cl | — | — |
| 3-26 | F | H | H | H | $CH_3$ | Q3 | $CH_3$ | $OCHF_2$ | Cl | — | — |
| 3-27 | F | H | H | $CH_3$ | $CH_3$ | Q3 | $CH_3$ | $OCHF_2$ | Cl | — | — |
| 3-28 | F | H | H | H | $CH_2CH_3$ | Q3 | $CH_3$ | $OCHF_2$ | Cl | — | — |
| 3-29 | F | H | H | $CH_2CH_3$ | $CH_2CH_3$ | Q3 | $CH_3$ | $OCHF_2$ | Cl | — | — |
| 3-30 | F | H | H | H | $CH_2Cl$ | Q3 | $CH_3$ | $OCHF_2$ | Cl | — | — |
| 3-31 | F | H | H | H | $CH_2OCH_3$ | Q3 | $CH_3$ | $OCHF_2$ | Cl | — | — |
| 3-32 | F | H | H | H | $CH=CH_2$ | Q3 | $CH_3$ | $OCHF_2$ | Cl | — | — |
| 3-33 | F | H | H | H | phenyl | Q3 | $CH_3$ | $OCHF_2$ | Cl | — | — |
| 3-34 | F | H | H | phenyl | phenyl | Q3 | $CH_3$ | $OCHF_2$ | Cl | — | — |
| 3-35 | F | $CH_3$ | H | H | H | Q3 | $CH_3$ | $OCHF_2$ | Cl | — | — |
| 3-36 | F | H | H | H | H | Q3 | $CH_3$ | $OCHF_2$ | Br | — | — |
| 3-37 | F | H | H | H | H | Q2 | — | — | — | — | — |
| 3-38 | F | H | H | H | $CH_3$ | Q2 | — | — | — | — | — |
| 3-39 | F | H | H | $CH_3$ | $CH_3$ | Q2 | — | — | — | — | — |
| 3-40 | F | H | H | H | $CH_2CH_3$ | Q2 | — | — | — | — | — |
| 3-41 | F | H | H | $CH_2CH_3$ | $CH_2CH_3$ | Q2 | — | — | — | — | — |
| 3-42 | F | H | H | H | $CH_2Cl$ | Q2 | — | — | — | — | — |
| 3-43 | F | H | H | H | $CH_2OCH_3$ | Q2 | — | — | — | — | — |
| 3-44 | F | H | H | H | $CH=CH_2$ | Q2 | — | — | — | — | — |
| 3-45 | F | H | H | H | phenyl | Q2 | — | — | — | — | — |
| 3-46 | F | H | H | phenyl | phenyl | Q2 | — | — | — | — | — |
| 3-47 | F | $CH_3$ | H | H | H | Q2 | — | — | — | — | — |

Table 4 lists some of the characterization data for a few representative compounds of this invention.

TABLE 4

$^1$H NMR data

| No. | NMR ($CDCl_3$, 300 MHz) ppm |
|---|---|
| 1-1 | 3.55(3H, s), 4.30(1H, d, J=18.4Hz), 4.41(1H, d, J=18.4Hz), 4.71(2H, s), 6.36(1H, s), 6.65 (1H, d, J=9.6Hz), 10.31(1H, s) |
| 1-2 | 1.30(3H, m), 3.44(3H, s), 4.77(2H, m), 4.91(1H, m), 6.60, 6.63(1H, each s), 6.91, 6.93 (1H, each d, J=10.2Hz), 10.98, 11.01(1H, each s) |
| 1-4 | $(CD_3)_2SO$ 0.81(3H, m), 1.72(2H, m), 3.43(3H, s), 4.70–4.90(3H, m), 6.60, 6.62(1H, each s), 6.91, 6.93(1H, each d, J=10.2Hz), 11.01, 11.05(1H, each s) |
| 1-13 | 4.11(3H, s), 4.55(2H, s), 4.73(2H, s), 6.61(1H, d, J=9.9Hz), 8.45(1H, s) |
| 1-15 | 1.94(6H, s), 4.10(3H, s), 4.61(2H, s), 6.55(1H, d, J=9.8Hz), 8.27(1H, s) |
| 1-21 | 4.08(3H, s), 4.65(1H, d, J=15.0Hz), 4.83(1H, d, J=15.0Hz), 6.25(1H, s), 6.67(1H, d, J=9.9Hz), 7.32(br s, 5H), 8.58(1H, s) |
| 1-25 | 3.88(3H, s), 4.54(2H, s), 4.72(2H, s), 6.59(1H, d, J=10.1Hz), 6.74(1H, t, J=72.1Hz), 8.90 (1H, s) |
| 1-26 | 1.48(3H, d, J=7.0Hz), 3.88(3H, s), 4.56(1H, d, J=14.8Hz), 4.78(1H, d, J=14.8Hz), 5.25 (1H, m), 6.60(1H, d, J=10.0 Hz), 6.75(1H, t, J=72.1Hz), 8.90(1H, s) |
| 1-27 | 1.94(6H, s), 3.87(3H, s), 4.60(2H, s), 6.53(1H, d, J=9.9Hz), 6.75(1H, t, J=72.1Hz), 8.76 (1H, s) |
| 1-28 | 0.97(3H, t, J=7.5Hz), 1.88(2H, m), 3.88(3H, s), 4.55(1H, d, J=14.9Hz), 4.81(1H, d, J=14.9Hz), 5.17(1H, t, J=6.6Hz), 6.61(1H, d, J=10.1Hz), 6.75(1H, t, J=72.1Hz), 8.92 (1H, s) |
| 1-33 | 3.85(3H, s), 4.64(1H, d, J=15.0Hz), 4.82(1H, d, J=15.0Hz), 6.24(1H, s), 6.65(1H, d, J=10.1Hz), 6.73(1H, t, J=72.1Hz), 7.32(5H, br s), 9.09(1H, s) |

TABLE 4-continued

¹H NMR data

| No. | NMR (CDCl₃, 300 MHz) ppm |
|---|---|
| 1-37 | (CD₃)₂SO 1.75(4H, m), 2.34(4H, m), 4.40(2H, s), 4.78(2H, s), 6.86(1H, d, J=10.2Hz), 10.99(1H, s) |
| 1-38 | CDCl₃+CD₃OD 1.48(3H, d, J=6.9Hz), 1.87(4H, m), 2.45(4H, m), 4.60(1H, d, J=14.8Hz), 4.77(1H, d, J=14.8Hz), 5.13(1H, m), 6.64(1H, d, J=9.7Hz), 7.49(1H, s) |
| 1-48 | 1.64(3H, d, J=6.8Hz), 4.11(3H, s), 4.40(1H, d, J=18.2Hz), 4.63(1H, d, J=18.2Hz), 4.77 (1H, q, J=6.7Hz), 6.61(1H, d, J=9.9Hz), 8.43(1H, s) |
| 1-50 | 1.46(m) and 1.71(d, J=6.6Hz) (6H combined), 4.11(3H, s), 4.57(q) and 4.94(q) (1H combined), 5.21(1H, m), 6.62(1H, pair of d), 8.42(1H, s) |
| 1-52 | (CD₃)₂SO 1.48(6H, s), 4.03(3H, s), 4.37(2H, s), 6.79(1H, d, J=10.0Hz), 10.13(1H, s) |
| 1-53 | 1.03(6H, m), 1.50 and 1.78(3H combined, m), 2.13(1H, m), 4.16(3H, s), 4.59 and 5.04(2H, each m), 6.68(1H, d, J=9.8Hz), 8.47(1H, br s) |
| 1-54 | (CD₃)₂SO 1.30(3H, d, J=7.0Hz), 1.35(3H, s), 1.61(3H, s), 4.04(3H, s), 4.85(1H, q, J=7.0 Hz), 6.84(1H, d, J=10.1Hz), 10.24(1H, s) |
| 1-55 | (CD₃)₂SO 1.49(3H, d, J=6.4Hz), 3.77(3H, s), 4.29(1H, d, J=17.5Hz), 4.47(1H, d, J=17.5 Hz), 4.89(1H, m), 6.82(1H, d, J=9.8Hz), 7.29(1H, t, J=71.1Hz), 9.93(1H, s) |
| 1-57 | (CD₃)₂SO 1.20–1.60(6H, m), 3.78(3H, s), 4.80–5.10(2H, m), 6.85(1H, m), 7.30(1H, t, J=71.2Hz), 10.05(1H, m) |
| 1-59 | (CD₃)₂SO 1.48(6H, s), 3.77(3H, s), 4.36(2H, s), 6.77(1H, d, J=10.1Hz), 7.30(1H, t, J=71.2 Hz), 9.91(1H, s) |
| 1-60 | (CD₃)₂SO 1.30(3H, d, J=7.0Hz), 1.34(3H, s), 1.60(3H, s), 3.78(3H, s), 4.86(1H, m), 6.81 (1H, d, J=10.1Hz), 7.29(1H, t, J=71.3Hz), 10.03(1H, s) |
| 1-61 | (CD₃)₂SO 0.82(3H, t, J=7.5Hz), 1.34(3H, s), 1.62(3H, s), 1.63–1.80(2H, m), 3.78(3H, s), 4.81(1H, m), 6.81(1H, d, J=10.1Hz), 7.29(1H, t, J=71.2Hz), 10.09(1H, s) |
| 1-62 | 1.39(3H, d, J=7.0Hz), 2.83(3H, br s), 3.86(3H, s), 4.56(1H, d, J=14.4Hz), 4.77(1H, d, J=14.4Hz), 5.35(1H, m), 6.69(1H, d, J=9.5Hz), 6.73(1H, t, J=72.0Hz) |
| 1-63 | (CD₃)₂SO 4.36(1H, d, J=17.6Hz), 4.46(1H, d, J=17.6Hz), 4.80(1H, s), 6.86(1H, d, J=10.2 Hz), 8.63(1H, m), 9.05(1H, m), 10.33(1H, s) |
| 1-64 | (CD₃)₂SO 1.32(3H, m), 4.78(2H, m), 4.93(1H, m), 6.91(1H, d, J=10.2Hz), 8.64(1H, m), 9.07(1H, m), 10.45(1H, m) |
| 1-66 | (CD₃)₂SO 0.86(3H, m), 1.73(2H, m), 4.70–4.90(3H, m), 6.91(1H, d, J=10.2Hz), 8.64(1H, m), 9.08(1H, m), 10.49(1H, m) |
| 1-68 | (CD₃)₂SO 4.85(2H, m), 5.97(1H, m), 6.97(1H, m), 7.20–7.50(5H, m), 8.63(1H, m), 9.05 (1H, m), 10.67(1H, m) |
| 1-73 | (CD₃)₂SO 2.37(3H, s), 4.33(1H, d=17.0Hz), 4.47(1H, d, J=17.0Hz), 4.79(2H, s), 6.89(1H, d, J=10.3Hz), 7.50(1H, t, J=56.9Hz), 10.93(1H, s) |
| 1-74 | (CD₃)₂SO 1.33(3H, d, J=6.9Hz), 2.38(3H, s), 4.72(1H, d, J=14.7Hz), 4.82(1H, d, J=14.7 Hz), 4.93(1H, m), 6.94(1H, d, J=10.3Hz), 7.51(1H, t, J=56.9Hz), 11.01(1H, s) |
| 1-75 | (CD₃)₂SO 0.83(3H, t, J=7.4Hz), 1.75(2H, m), 2.38(3H, s), 4.60–4.90(3H, m), 6.95(1H, d, J=10.3Hz), 7.51(1H, t, J=56.9Hz), 11.06(1H, s) |
| 1-76 | (CD₃)₂SO 2.24(1H, m), 2.32(1H, m), 4.10(2H, m), 4.46(2H, s), 4.54(1H, m), 4.70(1H, m), 4.77(2H, s), 6.71(1H, d, J=9.9Hz), 11.10(1H, s) |
| 1-77 | 0.85–1.00(6H, m), 2.07(1H, m), 3.57(3H, m), 4.51(1H, m), 4.70–4.90(2H, m), 6.36(1H, m), 6.68(1H, d, J=9.6Hz), 10.49(1H, m) |
| 1-78 | 0.80–1.10(6H, m), 1.88(4H, m), 2.00–2.20(1H, m), 2.44(4H, m), 4.40–4.90(3H, m), 6.63 (1H, d, J=9.7Hz), 9.51(1H, m) |

Herbicidal Activity

The compounds of the present invention exhibit excellent herbicidal effects when used as an active ingredient of a herbicide. The herbicide can be used for a wide range of applications, for example on crop lands such as paddy fields, upland farms, orchards and mulberry fields, and non-crop lands such as forests, farm roads, playgrounds, and factory sites. The application method may be suitably selected for soil treatment application and foliar application.

The compounds of the present invention are capable of controlling noxious weeds including grass (gramineae) such as barnyardgrass (*Echinochloa crus-galli*), large crabgrass (*Digitaria sanguinalis*), green foxtail (*Setaria viridis*), goosegrass (*Eleusine indica* L.), wild oat (*Avena fatua* L.), Johnsongrass (*Sorghum halepense*), quackgrass (*Agropyron repens*), alexandergrass (*Brachiaria plantaginea*), paragrass (*Panicum purpurascen*), sprangletop (*Leptochloa chinensis*) and red sprangletop (*Leptochloa panicea*); sedges (or Cyperaceae) such as rice flatsedge (*Cyperus iria* L.), purple nutsedge (*Cyperus rotundus* L.), Japanese bulrush (*Scirpus Juncoides*), flatsedge (*Cyperus serotinus*), small-flower umbrellaplant (*Cyperus difformis*), slender spikerush (*Eleocharis acicularis*), and water chestnut (*Eleocharis kuroguwai*); alismataceae such as Japanese ribbon wapato (*Sagittaria pygmaea*), arrow-head (*Sagittaria trifolia*) and narrowleaf waterplantain (*Alisma canaliculatum*); pontederiaceae such as monochoria (*Monochoria vaginalis*) and monochoria species (*Monochoria korsakowii*); scrophulariaceae such as false pimpernel (*Lindernia pyxidaria*) and abunome (*Dopatrium Junceum*); lythraceae such as toothcup (*Rotala indica*) and red stem (*Ammannia multiflora*); and broadleaves such as redroot pigweed (*Amaranthus retroflexus*), velvetleaf (*Abutilon theophrasti*), morningglory (*Ipomoea hederacea*), lambsquarters (*Chenopodium album*), prickly sida (*Sida spinosa* L.), common purslane (*Portulaca oleracea* L.), slender amaranth (*Amaranthus viridis* L.), sicklepod (*Cassia obtusifolia*), black nightshade (*Solanum nigrum* L.), pale smartweed (*Polygonum Lapathifolium* L.), common chickweed (*Stellaria media* L.), common cocklebur (*Xanthium strumarium* L.), flexuous bittercress (*Cardamine flexuosa* WITH.), henbit (*Lamium amplexicaule* L.) and threeseeded copperleaf (*Acalypha australis* L.). Accordingly, it is useful for controlling noxious weeds non-selectively or selectively in the cultivation of a crop plant such as corn (*Zea mays* L.), soybean (*Glycine*

*max* Merr.), cotton (Gossypium spp.), wheat (Triticum spp.), rice (*Oryza sativa* L.), barley (*Hordeum vulgare* L.), oat (*Avena sativa* L.), sorgo (*Sorghum bicolor* Moench), rape (*Brassica napus* L.), sunflower (*Helianthus annuus* L.), sugar beet (*Beta vulgaris* L.), sugar cane (*Saccharum officinarum* L.), Japanese lawngrass (*Zoysia Japonica* stend), peanut (*Arachis hypogaea* L.) or flax (*Linum usitatissimum* L.).

For use as herbicides, the active ingredients of this invention are formulated into herbicidal compositions by mixing herbicidally active amounts with inert ingredients known to the art to facilitate either the suspension, dissolution or emulsification of the active ingredient for the desired use. The type of formulation prepared recognizes the facts that formulation, crop and use pattern all can influence the activity and utility of the active ingredient in a particular use. Thus for agricultural use the present herbicidal compounds may be formulated as water dispersible granules, granules for direct application to soils, water soluble concentrates, wettable powders, dusts, solutions, emulsifiable concentrates (EC), microemulsion, suspoemulsion, invert emulsion or other types of formulations depending on the desired weed targets, crops and application methods.

These herbicidal formulations may be applied to the target area (where suppression of unwanted vegetation is the objective) as dusts, granules or water or solvent diluted sprays. These formulation may contain as little as 0.1% to as much as 97% active ingredient by weight.

Dusts are admixtures of the active ingredient with finely ground materials such as clays (some examples include kaolin and montmorillonite clays), talc, granite dust or other organic or inorganic solids which act as dispersants and carriers for the active ingredient; these finely ground materials have an average particle size of less than 50 microns. A typical dust formulation will contain 1% active ingredient and 99% carrier.

Wettable powders are composed of finely ground particles which disperse rapidly in water or other spray carriers. Typical carriers include kaolin clays, Fullers earth, silicas and other absorbent, wettable inorganic materials. Wettable powders can be prepared to contain from 1 to 90% active ingredient, depending on the desired use pattern and the absorbability of the carrier. Wettable powders typically contain wetting or dispersing agents to assist dispersion in water or other carriers.

Water dispersible granules are granulated solids that freely disperse when mixed in water. This formulation typically consists of the active ingredient (0.1% to 95% active ingredient), a wetting agent (1–15% by weight), a dispersing agent (1 to 15% by weight) and an inert carrier (1–95% by weight). Water dispersible granules can be formed by mixing the ingredients intimately then adding a small amount of water on a rotating disc (said mechanism is commercially available) and collecting the agglomerated granules. Alternatively, the mixture of ingredients may be mixed with an optimal amount of liquid (water or other liquid) and passed through an extruder (said mechanism is commercially available) equipped with passages which allow for the formation of small extruded granules. Alternatively, the mixture of ingredients can be granulated using a high speed mixer (said mechanism is commercially available) by adding a small amount of liquid and mixing at high speeds to affect agglomeration. Alternatively, the mixture of ingredients can be dispersed in water and dried by spraying the dispersion through a heated nozzle in a process known as spray drying (spray drying equipment is commercially available). After granulation the moisture content of granules is adjusted to an optimal level (generally less than 5%) and the product is sized to the desired mesh size.

Granules are granulated solids that do not disperse readily in water, but instead maintain their physical structure when applied to the soil using a dry granule applicator. These granulated solids may be made of clay, vegetable material such as corn cob grits, agglomerated silicas or other agglomerated organic or inorganic materials or compounds such as calcium sulfate. The formulation typically consists of the active ingredient (1 to 20%) dispersed on or absorbed into the granule. The granule may be produced by intimately mixing the active ingredient with the granules with or without a sticking agent to facilitate adhesion of the active ingredient to the granule surface, or by dissolving the active ingredient in a solvent, spraying the dissolved active ingredient and solvent onto the granule then drying to remove the solvent. Granular formulations are useful where in-furrow or banded application is desired.

Emulsifiable concentrates (EC) are homogeneous liquids composed of a solvent or mixture of solvents such as xylenes, heavy aromatic naphthas, isophorone or other proprietary commercial compositions derived from petroleum distillates, the active ingredient and an emulsifying agent or agents. For herbicidal use, the EC is added to water (or other spray carrier) and applied as a spray to the target area. The composition of an EC formulation can contain 0.1% to 95% active ingredient, 5 to 95% solvent or solvent mixture and 1 to 20% emulsifying agent or mixture of emulsifying agents.

Suspension concentrate (also known as flowable) formulations are liquid formulations consisting of a finely ground suspension of the active ingredient in a carrier, typically water or a non-aqueous carrier such as an oil. Suspension concentrates typically contain the active ingredient (5 to 50% by weight), carrier, wetting agent, dispersing agent, anti-freeze, viscosity modifiers and pH modifiers. For application, suspension concentrates are typically diluted with water and sprayed on the target area.

Solution concentrates are solutions of the active ingredient (1 to 70%) in solvents which have sufficient solvency to dissolve the desired amount of active ingredient Because they are simple solutions without other inert ingredients such as wetting agents, additional additives are usually added to the spray tank mix before spraying to facilitate proper application.

Microemulsions are solutions consisting of the active ingredient (1 to 30%) dissolved in a surfactant or emulsifier, without any additional solvents. There are no additional solvents added to this formulation. Microemulsions are particularly useful when a low odor formulation is required such as in residential turfgrass applications.

Suspoemulsions are combinations of two active ingredients. One active ingredient is made as a suspension concentrate (1–50% active ingredient) and the second active is made as a emulsifiable concentrate (0.1 to 20%). A reason for making this kind of formulation is the inability to make an EC formulation of the first ingredient due to poor solubility in organic solvents. The suspoemulsion formulation allows for the combination of the two active ingredients to be packaged in one container, thereby minimizing packaging waste and giving greater convenience to the product user.

The herbicidal compounds of this invention may be formulated or applied with insecticides, fungicides, acaricides, nematicides, fertilizers, plant growth regulators or other agricultural chemicals. Certain tank mix additives, such as spreader stickers, penetration aids, wetting agents, surfactants, emulsifiers, humectants and UV protectants maybe added in amounts of 0.01% to 5% to enhance the biological activity, stability, wetting, spreading on foliage or uptake of the active ingredients on the target area or to improve the suspensibility, dispersion, redispersion, emulsifiability, UV stability or other physical or physicochemical property of the active ingredient in the spray tank, spray system or target area.

The compositions of the present invention may be used in admixture with or in combination with other agricultural chemicals, fertilizers, adjuvants, surfactants, emulsifiers, oils, polymers or phytotoxicity-reducing agents such as herbicide safeners. In such a case, they may exhibit even better effects or activities. As other agricultural chemicals, herbicides, fungicides, antibiotics, plant hormones, plant growth regulators, insecticides, or acaricides may, for example, be mentioned. Especially with herbicidal compositions having the compounds of the present invention used in admixture with or in combination with one or more active ingredients of other herbicides, it is possible to improve the herbicidal activities, the range of application time(s) and the range of applicable weed types. Further, the compounds of the present invention and an active ingredient of another herbicide may be separately formulated so they may be mixed for use at the time of application, or both may be formulated together. The present invention covers such herbicidal compositions.

The blend ratio of the compounds of the present invention with the active ingredient of other herbicides can not generally be defined, since it varies depending on the time and method of application, weather conditions, soil type and type of formulation. However one active ingredient of other herbicide may be incorporated usually in an amount of 0.01 to 100 parts by weight, per one part by weight of the compounds of the present invention. Further, the total dose of all of the active ingredients is usually from 1 to 10000 g/ha, preferably from 5 to 500 g/ha The present invention covers such herbicidal compositions.

As the active ingredients of other herbicides, the following (common name) may be mentioned. Herbicidal compositions having the compounds of the present invention used in combination with other herbicides, may occasionally exhibit a synergistic effect.

Those that are believed to exhibit herbicidal effects by disturbing auxin activities of plants, including a phenoxy acetic acid type such as 2,4-D, 2,4-DB, 2,4-DP, MCPA, MCPP, MCPB or naproanilide (including the free acids, esters or salts thereof), an aromatic carboxylic type such as 2,3,6 TBA, dicamba, dichlobenil, a pyridine type such as picloram (including free acids and salts thereof), triclopyr or clopyralid and others such as naptalam, benazolin, quinclorac, quinmerac or diflufenzopyr (BAS 654H).

Those that are believed to exhibit herbicidal effects by inhibiting photosynthesis of plants including a urea type such as diuron, linuron, isoproturon, chlorotoluron, metobenzuron, tebuthiuron or fluometuron, a triazine type such as simazine, atrazine, cyanazine, terbuthylazine, atraton, hexazinone, metribuzin, simetryn, ametryn, prometryn, dimethametryn or triaziflam, a uracil type such as bromacil, terbacil or lenacil, an anilide type such as propanil or cypromid, a carbamate type such as desmedipham or phenmedipham, a hydroxybenzonitrile type such as bromoxynil or ioxynil, and others such as pyridate, bentazon and methazole.

A quaternary ammonium salt type such as paraquat, diquat or difenzoquat, which is believed to be converted to free radicals by itself to form active oxygen in the plant and thus to exhibit quick herbicidal effects.

Those which are believed to exhibit herbicidal effects by inhibiting chlorophyll biosynthesis in plants and abnormally accumulating a photsensitizing substance in the plant body, including a diphenyl ether type such as nitrofen, lactofen, acifluorfen-sodium, oxyfluorfen, fomesafen, bifenox, or chlomethoxyfen, a cyclic imide type such as chlorphthalim, flumioxazin, cinidon-ethyl, or flumiclorac-pentyl, and others such as oxadiazon, sulfentrazone, thidiazimin, azafenidin, carfentrazone, isopropazole, fluthiacet-methyl, pentoxazone, pyraflufen-ethyl and oxadiargyl.

Those which are believed to exhibit herbicidal effects characterized by whitening activities by inhibiting chromogenesis of plants such as carotenoids including a pyridazinone type such as norflurazon, chloridazon or metflurazon, a pyrazol type such as pyrazolate, pyrazoxyfen or benzofenap, and others such as fluridone, fluramone, diflufencam, methoxyphenone, clomazone, amitrole, sulcotrione, mesotrione, isoxaflutole and isoxachlortole.

Those which exhibit herbicidal effects specifically to gramineous plants including an aryloxyphenoxypropionic acid type (either as a mixture of isomers or as a resolved isomer) such as diclofop-methyl, pyrofenop-sodium, fluazifop butyl or fluazifop-p-butyl, haloxyfopmethyl, quizalofop-pethyl, quizalafop p-tefuryl, fenoxaprop ethyl or fenoxaprop-p-ethyl, flamprop-M-methyl or flamprop-m-isopropyl or cyhalofop-butyl and a cyclohexanedione type such as alloxydim-sodium, sethoxydim, clethodim, tepraloxydim or tralkoxydim.

Those which are believed to exhibit herbicidal effects by inhibiting amino acid biosynthesis of plants, including a sulfonylurea type such as chlorimuron-ethyl, nicosulfuron, metsulfuron-methyl, triasulfuron, primisulfuron, tribenuron-methyl, chlorosulfuron, bensulfuron-methyl, sulfometuron-methyl, prosulfuron, halosulfuron or halosulfuron-methyl, thifensulfuron-methyl, rimsulfuron, azimsulfuron, flazasulfuron, imazosulfuron, cyclosulfamuron, flupyrsulfuron, iodosulfuron, ethoxysulfuron, flucarbazone, sulfosulfuron, oxasulfuron a triazolopyrimidinesulfonamide type such as flumetsulam, metosulam, chioransulam or chloransulam-methyl, an imidazolinone type such as imazapyr, imazethapyr, imazaquin, imazamox, imazarmeth, imazamethabenz methyl, a pyrimidinesalicylic acid type such as pyrthiobac-sodium, bispyribac-sodium, pyriminobac-methyl or pyribenzoxim (LGC-40863), and others such as glyphosate, glyphosate-ammonium, glyphosate-isopropylamine or sulfosate.

Those which are believed to exhibit herbicidal effects by interfering with the normal metabolism of inorganic nitrogen assimilation such as glufosinate, glufosinate-ammonium, phosphinothricin or bialophos.

Those which are believed to exhibit herbicidal effects by inhibiting cell division of plant cells, including a dinitroaniline type such as trifluralin, oryzalin, nitralin, pendamethalin, ethafluralin, benefin and prodiamine, an amide type such as bensulide, napronamide, and pronamide, a carbarnate type such as propham, chlorpropham, barban, and asulam, an organophosphorous type such as aminoprofos-methyl or butamifos and others such as DCPA and dithiopyr.

Those which are believed to exhibit herbicidal effects by inhibiting protein synthesis of plant cells, including a chloroacetanilide type such as alachlor, metolachor (including combinations with safeners such as benoxacor, or resolved isomeric mixtures of metolachlor including safeners such as benoxacor) propachlor, acetochlor (including combinations with herbicide safeners such as dichlormid or MON 4660 or resolved isomeric mixtures of acetochlor containing safeners such as dichlornid or MON 4660), propisochlor or dimethenarmid or an oxyacetamide type such as flufenacet.

Those in which the mode of action causing the herbicidal effects are not well understood including the dithiocarbamates such as thiobencarb, EFITC, diallate, triallate, molinate, pebulate, cycloate, butylate, vemrolate or prosulfocarb and miscellaneous herbicides such as MSMA, DSMA, endothall, ethofumesate, sodium chlorate, pelargonic acid and fosamine. A few formulation examples of the present invention are given as follows:

Pella 86, SOY), upland rice (Oryza sp., var.Tebonnet, RICE), and wheat (*Triticum aestivum*) were included all plants were grown in 10 cm square plastic pots which were filled with a sandy loam soil mix.

Pre-emerge Test

For pre-emerge tests, seeds were planted one day prior to application of the test compounds. All test compounds were dissolved in acetone and applied to the test pots in a volume of 187 l/ha. Test materials were applied at rates ranging from 8 g ai/ha to 1000 g ai/ha using a track sprayer equipped with a TJ8001E even flow flat fan spray nozzle. This application simulates a typical commercial field herbicide application.

Post-emerge Test

| Ingredient Trade Name | Chemical Name | Supplier | Function | % wt./wt. |
|---|---|---|---|---|
| Formulation example 1. Emulsifiable Concentrate | | | | |
| | | | Active Ingredient | 5.0 |
| Toximul H-A | Calcium sulfonate and nonionic surfactant blend | Stepan Co. | Emulsifier | 2.5 |
| Toximul D-A | Calcium sulfonate and nonionic surfactant blend | Stepan Co. | Emulsifier | 7.5 |
| Aromatic 200 | Aromatic hydrocarbon | Exxon Chemical Co. | Solvent | QS to 100% |
| Formulation example 2. Suspension Concentrate | | | | |
| | | | Active Ingredient | 10.0 |
| Proylene glycol | | | Anti-freeze | 5.00 |
| Antifoam 1530 | Silicone defoamer | Dow Corning | Anti-foam | 0.50 |
| Rhodopol 23 | Xanthan gum | Rhone-Poulenc | Suspending Aid | 0.25 |
| Morwet D-425 | Naphthalene formaldehyde condensate | Witco Corp. | Dispersant | 3.00 |
| Igepal CA-720 | Octylphenol ethoxylate | Rhone-Poulenc | Wetting agent | 3.00 |
| Proxel GXL | 1,2 benziso-thiazolin-3-one | ICI Americas | Preservative | 0.25 |
| Water | | | Diluent | 68.00 |
| Formulation example 3. Wettable Powder | | | | |
| | | | Active Ingredient | 50.00 |
| Geropon T-77 | Sodium N-methyl-N-oleoyl taurate | Rhone-Poulenc | Wetting agent | 3.00 |
| Lomar PW | Naphthalene Sulfonate | Henkel Corp. | Dispersant | 5.00 |
| Kaolin clay | Kaolin clay | J. M. Huber | Filler | 42.00 |
| Formulation example 4. Water Dispersible Granule | | | | |
| | | | Active Ingredient | 50.00 |
| Morwet EFW | | Witco Corp. | Wetting agent | 2.00 |
| Morwet D-425 | Napthalene formaldehyde condensate | Witco Corp. | Dispersant | 10.00 |
| ASP 400 | Kaolin Clay | Engelhard Corp. | Filler | 38.00 |

Test Example

A standard greenhouse herbicide activity screening system was used to evaluate the herbicidal efficacy and crop safety of these test compounds. Seven broadleaf weed species including redroot pigweed (*Amaranthus retroflexus*, AMR), velvetleaf (*Abutilon theophrasti*, ABT), sicklepod (*Cassia obtusifolia*, CAO), ivyleaf morningglory (*Ipomoea hederacea*, IPH), lambsquarters (*Chenopodium album*, CHA), common ragweed (*Ambrosia artemisiifolia* L., AML), and cocklebur (*Xanthium strumariunt*, XAS) were used as test species. Four grass weed species including green foxtail (*Setaria viridis*, SEV), barnyardgrass (*Echinachloa crus-galli*, ECC), johnsongrass (*Sorghum halepense*, SOH), and large crabgrass (*Digitaria sanguinalis*, DIS) were also used. In addition, four crop species, field corn (*Zea mays* L., var. Dekalb 535, CORN), soybean (*Glycine max* L., var.

For post-emerge tests, seeds were planted 8–21 days prior to the test to allow emergence and good foliage development prior to application of the test substances. At the time of the post-emerge application, plants of all species were usually at the 2–3 leaf stage of development. In the postemerge test, a commercial non-ionic surfactant was also included (0.25% v/v) to enhance wetting of the leaf surfaces of target plants.

At 14 days after application of the test materials, phytotoxicity ratings were recorded. A rating scale of 0–100 was used for both pre and post emerge tests as previously described in *Research Methods in Weed Science*, 2nd edition, B, Truelove, Ed., Southern Weed Science Society, Auburn University, Auburn, Ala., 1977. Briefly, "0" corresponds to no damage and "100" corresponds to complete death of all plants in the test unit. This scale was used both to determine efficacy against weed species and damage to crop species. Herbicide activity data for various compounds of this invention, which are shown by compound No. in Tables 1–3, are shown in Tables 5 and 6. The data demonstrate significant differences between compounds for both efficacy against weeds and selectivity for crop species. For selected compounds, excellent activity against a majority of the weed species was observed with minimal damage to at least one of the crop species.

TABLE 5

Pre-emerge Herbicidal Activity

| Compd. No. | Rate g ai/ha | AMR | ABT | CAO | IPH | CHA | AML | XAS | SEV | ECC | SOH | DIS | CORN | SOY | RICE | WHEAT |
|---|---|---|---|---|---|---|---|---|---|---|---|---|---|---|---|---|
| 1-1 | 250 | 100 | 100 | 100 | 100 | 100 | 100 | 99 | 100 | 100 | 100 | 100 | 100 | 100 | 100 | 100 |
| 1-2 | 250 | 100 | 100 | 99 | 100 | 100 | 100 | 99 | 100 | 100 | 100 | 100 | 100 | 99 | 100 | 100 |
| 1-4 | 250 | 100 | 100 | 99 | 100 | 100 | 100 | 100 | 100 | 100 | 100 | 100 | 100 | 100 | 99 | 100 |
| 1-13 | 250 | 100 | 100 | 100 | 100 | 100 | 100 | 80 | 100 | 100 | 100 | 100 | 90 | 50 | 90 | 65 |
| 1-15 | 250 | 100 | 100 | 100 | 100 | 100 | 100 | 100 | 100 | 100 | 100 | 100 | 60 | 50 | 40 | 90 |
| 1-21 | 250 | 100 | 100 | 60 | 95 | 100 | 98 | 40 | 98 | 75 | 85 | 99 | 0 | 35 | 0 | 20 |
| 1-25 | 250 | 100 | 100 | 100 | 100 | 100 | 100 | 95 | 100 | 100 | 100 | 100 | 99 | 40 | 85 | 85 |
| 1-26 | 250 | 100 | 100 | 99 | 100 | 100 | 100 | 99 | 100 | 100 | 100 | 100 | 100 | 98 | 100 | 98 |
| 1-27 | 250 | 100 | 100 | 100 | 100 | 100 | 100 | 80 | 100 | 100 | 100 | 100 | 55 | 35 | 85 | 80 |
| 1-28 | 250 | 100 | 100 | 100 | 100 | 100 | 98 | 100 | 100 | 100 | 100 | 100 | 85 | 40 | 75 | 65 |
| 1-33 | 250 | 100 | 100 | 65 | 70 | 100 | 100 | 75 | 99 | 55 | 70 | 100 | 0 | 15 | 10 | 10 |
| 1-37 | 250 | 100 | 60 | 40 | 85 | 100 | 98 | 35 | 0 | 15 | 25 | 40 | 15 | 10 | 20 | 20 |
| 1-48 | 250 | 100 | 100 | 100 | 100 | 100 | 99 | 60 | 100 | 100 | 100 | 100 | 70 | 40 | 55 | 25 |
| 1-49 | 250 | 100 | 100 | 100 | 100 | 100 | 100 | 85 | 100 | 100 | 100 | 100 | 70 | 50 | 70 | 60 |
| 1-50 | 250 | 100 | 100 | 99 | 90 | 100 | 100 | 75 | 100 | 99 | 100 | 99 | 85 | 60 | 50 | 25 |
| 1-51 | 250 | 100 | 100 | 100 | 98 | 100 | 100 | 99 | 100 | 100 | 100 | 100 | 70 | 65 | 70 | 60 |
| 1-52 | 250 | 100 | 100 | 97 | 95 | 100 | 98 | 85 | 90 | 85 | 100 | 80 | 50 | 50 | 0 | 0 |
| 1-53 | 250 | 100 | 100 | 100 | 95 | 100 | 95 | 100 | 99 | 95 | 90 | 98 | 25 | 50 | 5 | 15 |
| 1-54 | 250 | 100 | 100 | 99 | 75 | 100 | 95 | 90 | 98 | 85 | 99 | 95 | 55 | 55 | 0 | 0 |
| 1-55 | 250 | 100 | 99 | 100 | 100 | 100 | 100 | 95 | 100 | 100 | 100 | 100 | 20 | 60 | 40 | 3 |
| 1-56 | 250 | 100 | 100 | 100 | 100 | 100 | 100 | 100 | 100 | 100 | 100 | 100 | 50 | 15 | 75 | 55 |
| 1-57 | 250 | 100 | 100 | 100 | 100 | 100 | 100 | 95 | 100 | 100 | 100 | 100 | 50 | 50 | 65 | 35 |
| 1-59 | 250 | 100 | 100 | 99 | 85 | 100 | 100 | 60 | 100 | 99 | 100 | 99 | 40 | 15 | 50 | 45 |
| 1-60 | 250 | 100 | 100 | 98 | 100 | 100 | 80 | 85 | 100 | 100 | 100 | 100 | 80 | 40 | 70 | 50 |
| 1-61 | 250 | 100 | 100 | 65 | 98 | 100 | 80 | 60 | 100 | 99 | 100 | 98 | 0 | 25 | 10 | 15 |
| 1-62 | 250 | 65 | 90 | 50 | 60 | 100 | 35 | 25 | 100 | 90 | 90 | 50 | 10 | 10 | 50 | 45 |
| 1-63 | 250 | 100 | 100 | 99 | 100 | 100 | 100 | 100 | 100 | 100 | 100 | 100 | 100 | 50 | 100 | 90 |
| 1-64 | 250 | 100 | 100 | 100 | 100 | 100 | 100 | 100 | 100 | 100 | 100 | 100 | 100 | 99 | 95 | 90 |
| 1-66 | 250 | 100 | 100 | 98 | 100 | 100 | 100 | 50 | 100 | 100 | 100 | 100 | 95 | 35 | 85 | 50 |
| 1-68 | 250 | 100 | 99 | 40 | 40 | 100 | 65 | 30 | 100 | 98 | 99 | 100 | 5 | 5 | 0 | 30 |
| 1-73 | 250 | 100 | 100 | 90 | 100 | 100 | 80 | 65 | 100 | 100 | 100 | 100 | 100 | 60 | 100 | 90 |
| 1-74 | 250 | 98 | 100 | 75 | 95 | 99 | 80 | 98 | 100 | 98 | 99 | 99 | 100 | 95 | 99 | 98 |
| 1-75 | 250 | 50 | 100 | 65 | 99 | 100 | 85 | 85 | 99 | 100 | 100 | 100 | 100 | 98 | 99 | 10 |
| 1-76 | 250 | 65 | 55 | 45 | 25 | 98 | 55 | 60 | 0 | 35 | 35 | 25 | 5 | 0 | 10 | 0 |
| 1-77 | 250 | 100 | 100 | 90 | 100 | 100 | 100 | 98 | 100 | 100 | 99 | 100 | 100 | 100 | 99 | 99 |
| 1-78 | 250 | 20 | 10 | 15 | 25 | 70 | 0 | 0 | 0 | 0 | 0 | 0 | 0 | 0 | 0 | 0 |
| 1-79 | 250 | 100 | 75 | 60 | 60 | 100 | 99 | 65 | 15 | 35 | 50 | 80 | 30 | 40 | 30 | 30 |

TABLE 6

Post-emerge Herbicidal Activity

| Compd. No. | Rate g ai/ha | AMR | ABT | CAO | IPH | CHA | AML | XAS | SEV | ECC | SOH | DIS | CORN | SOY | RICE | WHEAT |
|---|---|---|---|---|---|---|---|---|---|---|---|---|---|---|---|---|
| 1-1 | 250 | 100 | 100 | 40 | 100 | 98 | 65 | 100 | 95 | 60 | 25 | 0 | 0 | 95 | 99 | 25 |
| 1-2 | 250 | 90 | 100 | 0 | 90 | 80 | 65 | 75 | 60 | 60 | 20 | 0 | 10 | 50 | 70 | 25 |
| 1-4 | 250 | 0 | 100 | 0 | 90 | 99 | 80 | 90 | 60 | 50 | 15 | 0 | 0 | 60 | 75 | 25 |
| 1-13 | 250 | 100 | 100 | 100 | 100 | 100 | 100 | 100 | 100 | 99 | 100 | 55 | 25 | 100 | 99 | 25 |
| 1-15 | 250 | 100 | 100 | 99 | 100 | 100 | 98 | 100 | 99 | 99 | 55 | 50 | 35 | 100 | 80 | 50 |
| 1-21 | 250 | 95 | 75 | 5 | 75 | 99 | 75 | 80 | 50 | 25 | 0 | 0 | 10 | 25 | 55 | 45 |
| 1-25 | 250 | 100 | 100 | 100 | 100 | 100 | 99 | 100 | 100 | 95 | 60 | 60 | 35 | 100 | 100 | 60 |
| 1-26 | 250 | 100 | 100 | 100 | 100 | 100 | 99 | 100 | 100 | 99 | 80 | 40 | 40 | 100 | 90 | 60 |
| 1-27 | 250 | 100 | 100 | 100 | 100 | 100 | 100 | 98 | 100 | 100 | 100 | 75 | 60 | 60 | 100 | 90 | 75 |
| 1-28 | 250 | 100 | 100 | 100 | 100 | 100 | 100 | 100 | 100 | 99 | 80 | 15 | 25 | 100 | 100 | 50 |
| 1-33 | 250 | 99 | 100 | 60 | 98 | 99 | 70 | 70 | 95 | 65 | 65 | 25 | 25 | 60 | 95 | 65 |
| 1-37 | 250 | 100 | 100 | 15 | 100 | 85 | 70 | 95 | 75 | 60 | 50 | 0 | 35 | 55 | 80 | 10 |
| 1-48 | 250 | 100 | 100 | 65 | 100 | 100 | 80 | 100 | 98 | 95 | 30 | 50 | 10 | 65 | 60 | 0 |
| 1-49 | 250 | 100 | 100 | 100 | 100 | 100 | 80 | 100 | 100 | 100 | 65 | 99 | 35 | 80 | 85 | 50 |
| 1-50 | 250 | 100 | 100 | 75 | 100 | 100 | 70 | 100 | 70 | 99 | 55 | 70 | 20 | 75 | 65 | 35 |
| 1-51 | 250 | 100 | 100 | 100 | 100 | 100 | 85 | 100 | 100 | 100 | 80 | 90 | 50 | 60 | 75 | 60 |
| 1-52 | 250 | 100 | 100 | 50 | 70 | 100 | 60 | 75 | 0 | 50 | 0 | 0 | 0 | 0 | 0 | 0 |
| 1-53 | 250 | 100 | 100 | 50 | 100 | 100 | 75 | 100 | 60 | 70 | 0 | 0 | 5 | 20 | 0 | 10 |
| 1-54 | 250 | 80 | 100 | 40 | 60 | 99 | 80 | 65 | 65 | 0 | 0 | 0 | 0 | 45 | 0 | 0 |
| 1-55 | 250 | 100 | 100 | 99 | 100 | 100 | 85 | 100 | 99 | 95 | 50 | 35 | 15 | 75 | 75 | 50 |
| 1-56 | 250 | 100 | 100 | 100 | 100 | 100 | 100 | 100 | 100 | 100 | 85 | 100 | 20 | 100 | 99 | 30 |

TABLE 6-continued
Post-emerge Herbicidal Activity
| Compd. No. | Rate g ai/ha | AMR | ABT | CAO | IPH | CHA | AML | XAS | SEV | ECC | SOH | DIS | CORN | SOY | RICE | WHEAT |
|---|---|---|---|---|---|---|---|---|---|---|---|---|---|---|---|---|
| 1-57 | 250 | 100 | 100 | 100 | 100 | 100 | 80 | 100 | 99 | 80 | 40 | 10 | 10 | 100 | 65 | 50 |
| 1-59 | 250 | 100 | 100 | 70 | 100 | 100 | 80 | 100 | 99 | 99 | 65 | 99 | 10 | 45 | 55 | 35 |
| 1-60 | 250 | 85 | 100 | 60 | 100 | 100 | 70 | 85 | 95 | 98 | 0 | 0 | 5 | 50 | 0 | 30 |
| 1-61 | 250 | 75 | 98 | 30 | 100 | 99 | 60 | 90 | 85 | 35 | 20 | 0 | 3 | 25 | 30 | 30 |
| 1-62 | 250 | 99 | 80 | 35 | 75 | 100 | 90 | 65 | 60 | 30 | 0 | 30 | 0 | 0 | 70 | 50 |
| 1-63 | 250 | 100 | 100 | 50 | 100 | 100 | 45 | 100 | 100 | 100 | 99 | 80 | 20 | 100 | 75 | 30 |
| 1-64 | 250 | 100 | 100 | 85 | 100 | 100 | 95 | 100 | 100 | 100 | 85 | 40 | 5 | 100 | 0 | 15 |
| 1-66 | 250 | 100 | 100 | 75 | 100 | 100 | 80 | 100 | 98 | 100 | 75 | 95 | 10 | 100 | 100 | 30 |
| 1-68 | 250 | 100 | 80 | 0 | 60 | 100 | 40 | 60 | 0 | 0 | 0 | 0 | 10 | 10 | 0 | 0 |
| 1-73 | 250 | 30 | 65 | 0 | 55 | 90 | 50 | 40 | 50 | 0 | 0 | 0 | 0 | 60 | 75 | 0 |
| 1-74 | 250 | 60 | 55 | 0 | 0 | 65 | 55 | 10 | 65 | 0 | 0 | 0 | 0 | 0 | 0 | 0 |
| 1-75 | 250 | 0 | 90 | 0 | 80 | 80 | 45 | 20 | 0 | 0 | 0 | 0 | 0 | 55 | 40 | 0 |
| 1-76 | 250 | 0 | 0 | 0 | 0 | 0 | 0 | 0 | 0 | 0 | 0 | 0 | 0 | 0 | 0 | 0 |
| 1-77 | 250 | 25 | 50 | 0 | 75 | 90 | 0 | 50 | 0 | 0 | 0 | 0 | 0 | 10 | 35 | 0 |
| 1-78 | 250 | 60 | 0 | 0 | 75 | 99 | 70 | 80 | 0 | 0 | 0 | 0 | 0 | 10 | 60 | 50 |
| 1-79 | 250 | 70 | 75 | 0 | 60 | 65 | 80 | 0 | 65 | 25 | 0 | 0 | 0 | 0 | 0 | 0 |
What is claimed is:
1. A compound represented by the formula (I) or its salt:
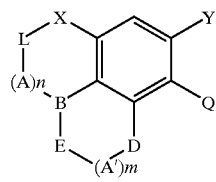
I
wherein Q is a heterocycle selected from the group consisting of QI to Q24:
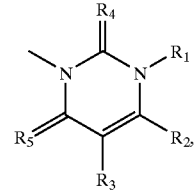
Q1
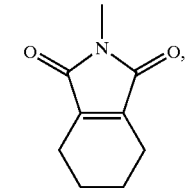
Q2
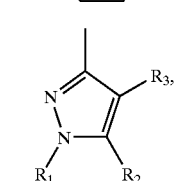
Q3
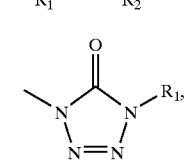
Q4
-continued
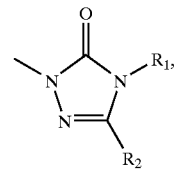
Q5
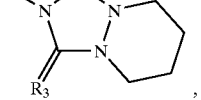
Q6
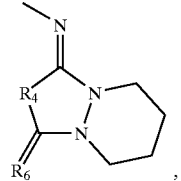
Q7
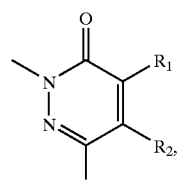
Q8
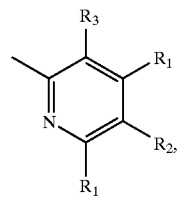
Q9

-continued

Q10 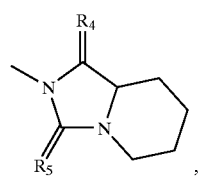

Q11 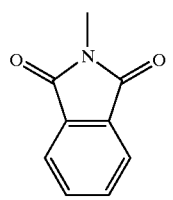

Q12 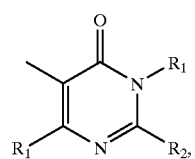

Q13 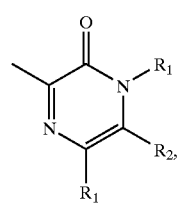

Q14 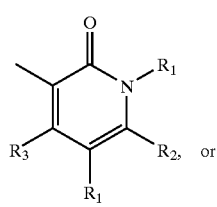 or

Q15 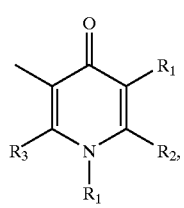

Q16 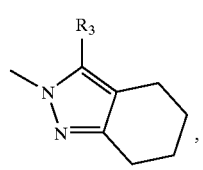

Q17 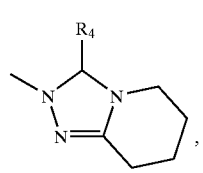

-continued

Q18 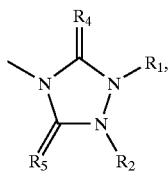

Q19 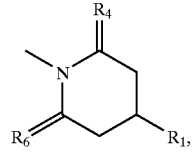

Q20 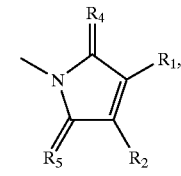

Q21 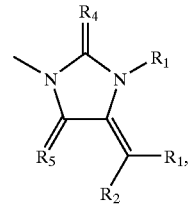

Q22 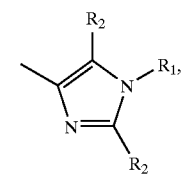

Q23 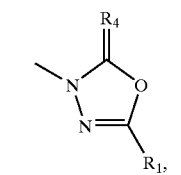

Q24 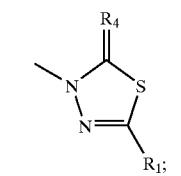

wherein $R_1$ is hydrogen, alkyl, haloalkyl, alkenyl, alkynyl, amino, alkoxyalkyl, acetyl, alkoxycarbonylamino or alkoxycarbonyl;

$R_2$ is alkyl, haloalkyl, alkoxy, haloalkoxy or unsubstituted or substituted phenyl;

$R_3$ is hydrogen, halogen, nitro, amino, alkylamino, haloalkylamino, cyano or amide;

$R_4$ and $R_5$ are independently oxygen, sulfur or imino; Q6, Q7, Q10, Q16 or Q17 may be unsaturated containing one or two double bonds in the 6-membered ring;

Y is hydrogen or halogen;

—L—X— is —CR$_6$R$_7$—O, or —CR$_6$R$_7$—S—,
A is —C(O)—;
A' is —C(O)—;
n is an integer of 1;
m is an integer of 1;
B is N;
E is —CR$_{12}$R$_{13}$,—
D is —NR—,
R$_6$ and R$_7$ are independently hydrogen or alkyl;
R$_{12}$, and R$_{13}$, are independently hydrogen, alkyl, alkenyl, or phenyl, heteroaryloxy, where any of these groups may be substituted with at least one substituent selected from the group consisting of halogen and alkoxy;
R is hydrogen, or alkyl.

2. The compound according to claim 1, wherein the formula (I) is

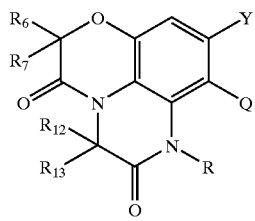

I-1

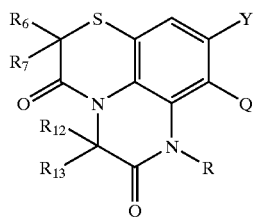

I-2

Wherein Q, R, R$_6$, R$_7$, R$_{12}$, R$_{13}$ and Y are the same as defined in claim 1.

3. The compound according to claim 1, wherein Q is Q 1–5, Q16 or Q17.

4. The compound according to claim 1, wherein Y is fluorine.

5. The compound according to claim 1, wherein the formula (I) is (I-1)

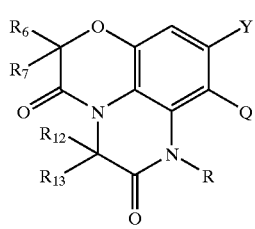

I-1

Wherein Q is Q1 or Q3; Y is fluorine; and R, R$_6$, R$_7$, R$_{12}$ and R$_{13}$ are the same as defined in claim 1.

6. The compound of claim 5, wherein the compound is 8-[1-Methyl-6-(trifluoromethyl)-2,4-(1H, 3H)-pyrimidinedione-3-yl]-9-fluoro-5H-pyrazino[1,2,3de]1,4-benzoxazine-3,6-(2H, 7H)-dione (1-1), 8-[4-Chloro-1-methyl-5-(trifluoromethyl)-1H-pyrazol-3-yl]-9-fluoro-5H-pyrazino[1,2,3-de]-1,4-benzoxazine-3,6(2H, 7H)-dione (1-13), 8-[4-Chloro-5-(difluoromethoxy)-1-methyl-1H-pyrazole-3-yl)-9-fluoro-5H-pyrazino[1,2,3-de]-1,4-benzoxazine-3,6(2H, 7H)-dione (1-25), 9-Fluoro-8-(4,5,6,7-tetrahydro-2H-isoindole-1,3-dione-2-yl)-5H-pyrazino[1,2,3de]-1,4-benzoxazine-3,6(2H, 7H)-dione (1-37), 8-[4-Chloro-1-methyl-5-(trifluoromethyl)-1H-pyrazol-3-yl]-9-fluoro-2R-methyl-5H-pyrazino[1,2,3dej-1,4-benzoxazine-3,6(2H, 7H)-dione(1-48), 8-[4-Chloro-1-methyl-5-trifluoromethyl)-1H-pyrazol-3-yl-2,2-dimethyl-9-fluoro-5H-pyrazino[1,2,3-de]-1,4-benzoxazine-3,6(2H, 7H)-dione (1-52) and 8-[4-Chloro-5(difluoromethoxy)-1-methyl-IH-pyrazole-3-y)-9-fluoro-2-R-methyl-5H-pyrazino[1,2,3de]-1,4-benzoxazine-3,6(2H, 7H)-dione (1-55).

7. A herbicidal composition, characterized in that it contains at least one compound according to claim 1 and an agricultural adjuvant.

8. A method for controlling undesired vegetation which comprises applying to a locus to be protected a herbicidally effective amount of a compound of claim 1.

9. The method of claim 8 wherein the locus to be protected is a cereal crop field.

10. The method of claim 8 wherein the compound of claim 1 is applied to soil as a preemergent herbicide.

11. The method of claim 8 wherein the compound of claim 1 is applied to plant foliage.

12. A process for preparing a compound represented by the formula (I') or its salt:

wherein Q is a heterocycle selected from the group consisting of Q1 to Q24:

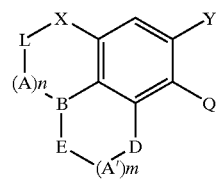

wherein Q is a heterocycle selected from the group consisting of Q1 to Q24:

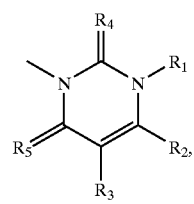

Q1

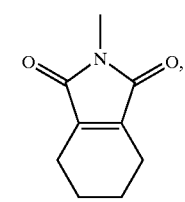

Q2

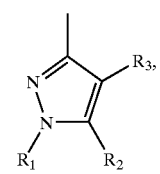

Q3

-continued
Q4 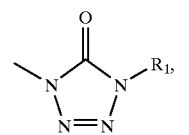
Q5 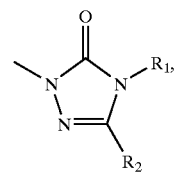
Q6 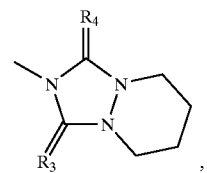
Q7 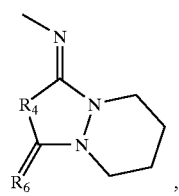
Q8 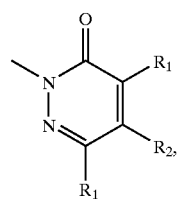
Q9 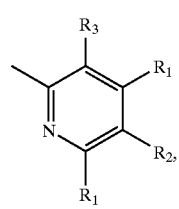
Q10 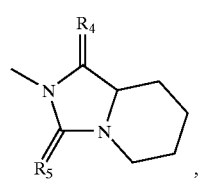
Q11 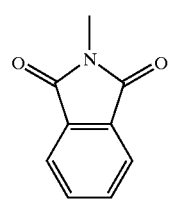
-continued
Q12 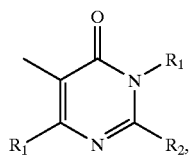
Q13 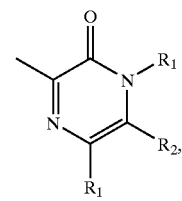
Q14 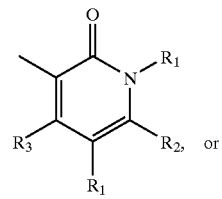 or
Q15 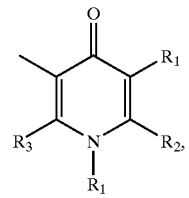
Q16 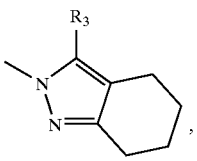
Q17 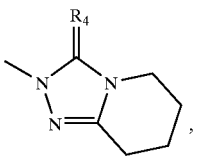
Q18 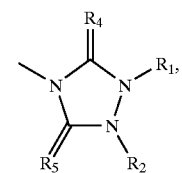
Q19 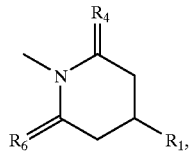

-continued

Q20 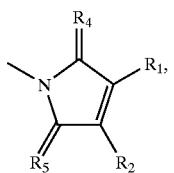

Q21 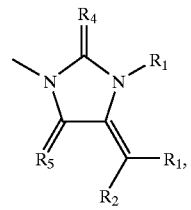

Q22 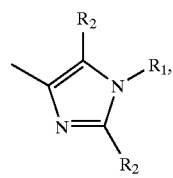

Q23 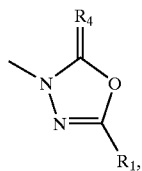

Q24 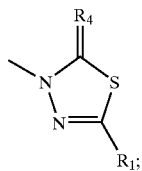

wherein $R_1$ is hydrogen, alkyl, haloalkyl, alkenyl, alkynyl, amino, alkoxyalkyl, acetyl, alkoxycarbonyl amino, alkylcarbonylamino or alkoxycarbonyl;

$R_2$ is alkyl, haloalkyl, alkoxy, haloalkoxy or unsubstituted or substituted phenyl;

$R_3$ is hydrogen, halogen, nitro, amino, alkylamino, haloalkylamino, cyan or amide;

$R_4$ and $R_5$ are independently oxygen, sulfur or imino; Q6, Q7, Q10, Q16 or Q17 may be unsaturated containing one or two double bonds in the 6-membered ring;

Y is hydrogen or halogen;

—L—X— is —$CR_6R_7$—O—, or —$CR_6R_7$—S—;

A is —C(O)—;

A' is —C(O)—;

n is an integer of 1;

m is an integer of 1;

B is N;

E is —$CR_{12}R_{13}$—;

D is —NR—;

$R_6$ and $R_7$ are independently hydrogen or alkyl;

$R_{12}$, and $R_{13}$, are independently hydrogen, alkyl, alkenyl, akenyl, or phenyl, where any of these groups may be substituted with at least one substituent selected from the group consisting of halogen, and alkoxy;

R is hydrogen or alkyl, which comprises of reacting a compound represented by the formula (II):

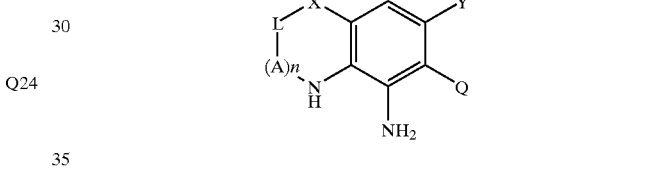

II with a compound selected from the group consisting of an appropriately substituted alkyl halide, alkyl acid halide, alkyl acid anhydride, aryl acid anhydride, alkyhaloformate, aryl isocyanate, alkyl dihalide, aliphatic aldehyde, aliphatic ketone, aromatic aldehyde, and aromatic ketone followed by cyclization.

* * * * *